US007400021B2

(12) United States Patent
Wu et al.

(10) Patent No.: US 7,400,021 B2
(45) Date of Patent: *Jul. 15, 2008

(54) THIN FILM OPTICAL DETECTORS FOR RETINAL IMPLANTATION AND METHODS FOR MAKING AND USING SAME

(75) Inventors: NaiJuan J. Wu, Pearland, TX (US); Ali Reza Zomorrodian, Houston, TX (US); Alex Ignatiev, Houston, TX (US)

(73) Assignee: The University of Houston System, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/475,307

(22) Filed: Jun. 27, 2006

(65) Prior Publication Data

US 2006/0240575 A1 Oct. 26, 2006

Related U.S. Application Data

(63) Continuation of application No. 10/480,890, filed as application No. PCT/US02/18734 on Jun. 15, 2002, now Pat. No. 7,067,327.

(51) Int. Cl.
*H01L 29/06* (2006.01)
(52) U.S. Cl. .................. 257/414; 257/451; 623/6.63
(58) Field of Classification Search .................. 607/54, 607/116; 257/414, 451; 623/6.63
See application file for complete search history.

(56) References Cited

U.S. PATENT DOCUMENTS 7,067,327 B2 * 6/2006 Wu et al. .................. 438/1

* cited by examiner

*Primary Examiner*—W. David Coleman
(74) *Attorney, Agent, or Firm*—Robert W. Strozier

(57) ABSTRACT

The present invention provides a method for capturing optical micro detectors for improved surgical handling during implantation into an eye comprising the steps of providing an optically active thin film heterostructure on a soluble substrate; forming an array comprising individual optical microdetectors from the optically active thin film heterostructure; attaching the optical microdetector array onto a biodegradable polymer carrier membrane; and separating the optical microdetector array attached to the biodegradable polymer carrier membrane from the soluble substrate thereby capturing the optical microdetectors in the bio-polymer carrier membrane for improved handling of the optical micro-detectors during transfer and implantation into the eye.

9 Claims, 20 Drawing Sheets

Output of ~ 250 m Thin Film Optical (TOD) illuminated with a light intensity of ~ 1mW/cm$^2$ Output of ~250 m Thin Film Optical Detector (TOD) Illuminated with a Variable Intensity ~ 1mW/cm² light source

THIN FILM OPTICAL DETECTORS FOR RETINAL IMPLANTATION AND METHODS FOR MAKING AND USING SAME

RELATED APPLICATIONS

This application is a continuation of U.S. patent application No. US Ser. No. 10/480,890 filed 12 Oct. 2004 now U.S. Pat. No. 7,067,327 issued 27 Jun. 2006, which is a United States Nationalization of PCT/US02/18734, filed 15 Jun. 2002.

BACKGROUND OF THE INVENTION

1. Field of the Invention

The present invention relates to medical optically active implants to treat blindness and method for implanting these implants into an animal including a human to allow detection of visible light by the blind or to repair damaged areas of the retina to allow the animal to retain visual acuity in the damages areas.

More particularly, the present invention relates to an implant including an array of optical microdetectors supported on or in a bio-absorbable substrate, where the microdetectors comprise a heterostructure. The present invention also relates to a method for making the implant, to a method for implanting the implant in an animal including a human and to methods for treating blindness, for replacing damaged retinal photo sensors and for ameliorating symptoms of diseases of the eye such as Retinitis Pigrnentosa (RP) and Age-related Macular degeneration (AMD).

2. Description of the Related Art

Recent efforts on external stimulation of retinal neuronal cells with electrical signals have resulted in visual brain sensation [1,3]. Several reports have established that stimulation of retinal neuronal cells with electrical signals can result in visual perception [2,15]. In view of this phenomenon, different approaches have been undertaken in order to restore the vision of a retinally blind person. This has been accomplished by either direct stimulation of the retina or direct retinal implant of an optical detector to stimulate retinal neuronal cells in a patient whose optical detectors are damaged [9,10,11,15]. Both epiretinal electrical stimulation [9,10] and retinal stimulation with implants placed in the subretinal space [11,15] have been investigated.

The implants can consist of an encapsulated micro-photodiode array with thousands of micro-contacts for localized electrical stimulation of the bipolar cells in the subretinal approach [11,15], or they can use external processing of visual information before it is sent to implanted electrodes in the epiretinal or subretinal space [9,10]. The latter systems utilize video cameras that capture the image and convert it to an electrical signal. The electrical signal is coded, then sent as telemetry to an implant receiver that decodes the signal and generates the desired current to stimulate retinal neurons.

By using a thin film optical device (TOD), it has been demonstrated that thin films of certain perovskite ferroelectric oxides show optical activities in the visible range of the electromagnetic spectrum [12]. These ceramic ferroelectric films are also shown to be stable in aqueous, basic or acidic solutions for long periods of time; while other photodetectors based on semiconductors require encapsulation and wire interconnects for integration into the eye.

Human photoreceptor topography studies indicate that the photoreceptors are in the shape of cones and rods, with different densities in different parts of the retina [4,5]. The photoreceptors are nominally hexagonally close-packed with receptor size varying between 2 to 5 microns.

Tissue or organ engineering develops functional devices such as microdetectors to substitute for the missing or malfunctioning tissues or organs in the human body. Bio-resorbable polymers that are fully degradable into the body's natural metabolites by simple hydrolysis under physiological conditions are the most desirable materials for the carrier of such functional substitutes in the human body.

Biodegradable polymers are well known as bio-materials for applications in cell transplantation and drug delivery [6,7]. In vitro dissolution of thin layers made from these polymers in simulated body fluid has been characterized in terms of film thickness, molecular weight and time of degradation [7,8]. Among these materials, poly (dl-lactic-co-glycolic acid) (PLGA) polymers have been widely utilized as a template for tissue and cell transplantation. This strategy is widely used and investigated for transplantation of many cells including retinal pigment epithelium (RPE). The disadvantage associated with these polymers is the time it takes to degrade which depends on the nature and, also, the thickness of the polymer.

Even though small microdetectors or other type of microdevices can be constructed using modern electronic fabrication techniques, the small size of such microdevices, which could approach the 5 micron size of human photo sensors, make the detector verifiably impossible to handle for individually implantation of such microdevices by current surgical techniques. Thus, surgical implantation is problematic for any micro-implantation of small devices, tissues or cell cultures.

Despite complex engineering issues, these different approaches for restoring vision in retinally blind people have led to encouraging preliminary results [2,15]. However, several questions need to be answered in order to better define the parameters influencing the optimal performance of such artificial retinas such as sensitivity, long-term stability, and the degree of spatial resolution that might be achieved by these devices. Moreover, the design of reliable and reasonably safe surgical procedures for implantation as well as biocompatibility and long term function of implanted devices still remain in the forefront of ongoing investigations.

The prior art is deficient in the lack of effective means of forming a surgically manipulable optical implant for replacement of damagee retinal photo sensor or for allowing the sightless to see. More specifically, the prior art is deficient in the lack of effective means for handling arrays of optical microdetector devices for implantation into the retina of the eye and for means of making suitable implants for implantation into the retina of an animal.

Thus, there is a need in the art for implants that can be handled using standard surgical techniques, for implants that include optical detectors distributed in a similar manner to the photoreceptors of an animal including a human eye and to methods for making such implants and implanting such implants.

SUMMARY OF THE INVENTION

Implants

The present invention provides an implant for communicating optical information to retinal neurons in an animal including a human, where the implant includes a bio-erodible carrier and an optically active, thin film, heterostructure optical microdetector, where the microdetector converts light energy into electrical energy sufficient to activate at least one bipolar cell of a retinal site, thus communicating optical information to retinal neurons for transmission to the brain. The term optical information means light of a sufficient intensity within a spectral range detectable by the microdetector.

The present invention also provides an implant for communicating optical information to retinal neurons in an animal including a human, where the implant includes a bio-erodible carrier and a plurality of optically active, thin film heterostructure optical microdetectors, where each microdetector converts light energy into electrical energy sufficient to activate bipolar cells of a retinal site, thus communicating optical information to retinal neurons for transmission to the brain.

The present invention also provides an implant for communicating optical information to retinal neuronal cells in an animal including a human, where the implant includes a bio-erodible carrier and a patterned plurality of optically active, thin film heterostructure optical microdetectors, where each microdetector converts light energy into electrical energy sufficient to activate bipolar cells of a retinal site for transmission of the optical information to the brain and where the pattern is designed to mimic a pattern of cones and/or rods in the retinal site.

The present invention also provides an implant for communicating optical information to retinal neurons in an animal including a human, where the implant includes a bio-erodible carrier and a patterned plurality of optically active, thin film heterostructure optical microdetectors, where the patterned microdetectors converts light energy into electrical energy sufficient to activate bipolar cells of a retinal site in a manner similar to how the cones and/or rods activate the bipolar cells in the retina.

The present invention also provides an implant for communicating optical information to retinal neurons in an animal including a human, where the implant includes a bio-erodible carrier including a first plurality of optically active, thin film heterostructure optical microdetectors sensitive to light in a low energy range or red range of the visible light energy range of the electromagnetic spectrum (RMDs), a second plurality of optically active, thin film heterostructure optical microdetectors sensitive to light in a medium energy range or green range of the visible light energy range of the electromagnetic spectrum (GMDs), a third plurality of optically active, thin film heterostructure optical microdetectors sensitive to light in a high energy range or blue range of the visible light energy range of the electromagnetic spectrum (BMDs), where the three microdetectors are arranged in a pattern with distributions of RMDs, GMDs and BMDs similar to a red, green, blue cone cell distributions in a retinal site into which the implant is to be implanted and where each microdetector converts light energy into electrical energy sufficient to activate bipolar cells in the retinal site.

Method for Making the Implants

The present invention provides a method for capturing optical microdetectors in an implant for improved surgical handling during implantation into an eye comprising the steps of: (1) forming an optically active thin film heterostructure on a top surface of a removable substrate; (2) patterning the thin film heterostructure to form an array comprising individual optically active, thin film, heterostructure microdetectors; (3) contacting the top surface of the substrate with the array thereon with a biodegradable polymer carrier; and (4) removing the removable substrate to form an implant comprising an array of optical microdetectors in a biodegradable polymer carrier, where the implant has improved surgical handling characteristics for implantation into the eye. The heterostructure can comprise a uniform composition or the heterostructure can comprise a pattern of different compositions, each composition absorbing light in a different region of the visible light spectrum. Preferably, the compositions include a red sensitive composition, a green sensitive composition and a blue sensitive compositions. The preferred distribution of compositions is a distribution that is similar to the distribution of red, green and blue sensitive cone cells in the retina of an animal that has color vision.

The present invention also provides a method for capturing optical microdetectors in an implant for improved surgical handling during implantation into an eye comprising the steps of: (1) depositing a conductive layer on a top surface of a removable substrate; (2) forming a first pattern on a surface of conductive layer using positive or negative photoresist lithograph; (3) depositing a first optically active material on exposed regions of the conductive layer to form a first thin film heterostructure of the top surface of the substrate, where the first heterostructure comprises the conductive layer and the first optically active layer and the first material is sensitive to light in a first region of the electromagnetic spectrum; (4) forming a second pattern on a surface of conductive layer using positive or negative photoresist lithograph; (5) depositing a second optically active material on exposed regions of the conductive layer to form a second thin film heterostructure of the top surface of the substrate, where the second heterostructure comprises the conductive layer and the second optically active layer and the second material is sensitive to light in a second region of the electromagnetic spectrum; (6) forming a second pattern on a surface of conductive layer using positive or negative photoresist lithograph; (7) depositing a third optically active material on exposed regions of the conductive layer to form a third thin film heterostructure of the top surface of the substrate, where the third heterostructure comprises the conductive layer and the third optically active layer and the third material is sensitive to light in a third region of the electromagnetic spectrum; (8) patterning the heterostructure using negative or positive photoresist lithography to form a patterned heterostructure; (9) removing those areas of the heterostructure not patterned during the negative or positive photoresist lithography to form an array of optical active microdetectors comprising pluralities of microdetectors composed of each of the three heterostructures on the top surface of the substrate; (10) forming a biodegradable polymer film onto the top surface of the substrate including the optical microdetector array thereon to secure each microdetector in the array to or in the film; and (11) removing the substrate to form an implant comprising an array of optical microdetectors in a biodegradable polymer carrier, where the implant has improved surgical handling characteristics for implantation into the eye. The three optical region can comprises a red, green and blue regions so that the heterostructures correspond to red, green and blue cone cells. Moreover, the three patterns can be constructed so that the distribution of red, green, and blue regions mimic the distribution found in the region of the retina in which the implant is intended. It should be obvious to an ordinary artisan that the formation of different optically active oxide layers to make different microdetectors can include additional compositions to allow detection of light in other regions of the electromagnetic spectrum.

Implanting the Implants

The present invention also provides a method for surgically implanting an optical implant into an eye of an animal including a human, the method comprising the steps of: implanting the optical implant of this invention at an implantation site in the eye so that the array of optical microdetectors within the implant are positioned to come into electrical contact with bipolar cells associated with the implant site after biodegradation of the biodegradable polymer carrier.

Other and further aspects, features, and advantages of the present invention will be apparent from the following description of the presently preferred embodiments of the invention given for the purpose of disclosure.

DESCRIPTION OF THE DRAWINGS

The invention can be better understood with reference to the following detailed description together with the appended illustrative drawings depicting non-limiting preferred embodiments of the implants of this invention in which like elements are numbered the same.

DETAILED DESCRIPTION OF THE INVENTION

Figure 1A:
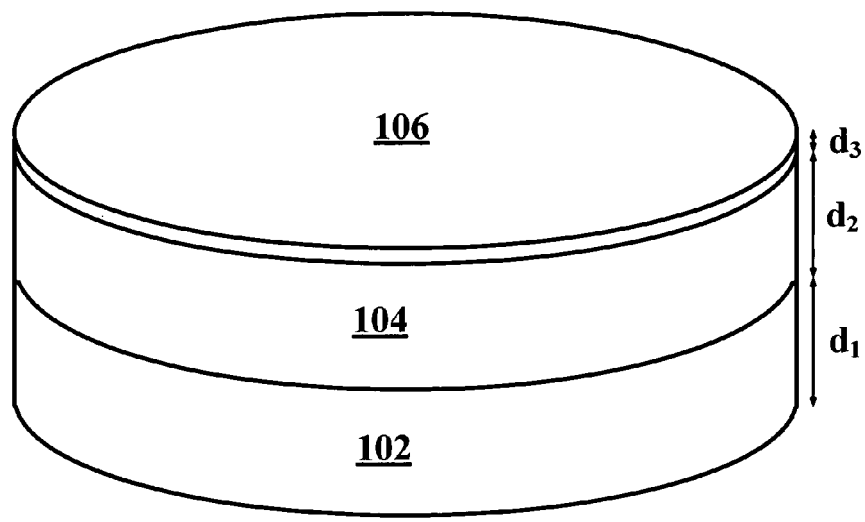
FIG. 1A depicts a schematic of a preferred embodiment of a thin film microdetector showing typical layer thicknesses and including an optional top electrode.

The present invention fulfills these long-standing needs and desires in the art. Thus, the inventors have found that optically active implants can be constructed that include a plurality of micro-optical detectors or optical microdetectors in or on a biodegradable carrier, where the implants can be handled using standard surgical techniques and the microdetectors are of a size and distributed in or on the carrier in a patterned configuration to facilitate activation of a majority of the bipolar cells in the site of retinal implantation. The inventors have found that a carrier, especially one that is biodegradable carrier, permits fabrication of implant with many micro-elements in an appropriate array configuration. The carrier along with the attached micro-devices, e.g., optical microdetectors, can be reliably implanted into the receiving entity. Preferably, each microdetector is of a size and shape to active only a small number of bipolar retinal cells and most preferably, where each microdetector is of a size and shape to active only a single bipolar cell in the retinal implantation site. Because the implant is of a size ideally suited for implantation using standard microsurgical techniques, optical implants can be directly implanted, without encapsulation, into the subretinal space to replace aged and/or diseased photoreceptors for restoration of sight in retinally blind people.

The ceramic thin film optical microdetector (TOD) of this invention were designed to address some of these issues. The oxide ceramics used as the optically active thin film element in the TOD belong to a class of polar crystals (ferroelectric oxides), which can generate a steady state voltage upon illumination in the absence of external fields [16]. This voltage, which can considerably exceed the band gap energy of the oxide, is due to the anomalous ferroelectric photovoltaic effect (APE), and is the result of a directional charge transfer from the localized states of the absorbing impurities in the oxides [17]. A high-voltage bulk photovoltaic effect has already been observed in a number of ferroelectric oxides such as $LiNbO_3$, doped $BaTiO_3$, and also doped $PbZrTiO_3$, with outputs ranging from 100 V to $10^5$ V depending on the thickness of the sample [16,17]. The APE voltage can be varied by the choice of material, doping, and growing a different thickness of the active layer to comply with the bionic-eye TOD requirement.

Although the implants of the present invention are designed to operate in the visible region of the electromagnetic spectrum, the implants can be constructed to include microdetectors that are sensitive to frequencies of light in other regions of the electromagnetic spectrum. Preferred other regions include light in the IR and near IR, light in the UV region such as near UV and far UV regions and even light in the X-ray region of the electromagnetic spectrum. Implants having the ability to detect light in non-visible regions of the electromagnetic spectrum could have application is improving the night view of guard animals such as dogs, improving the night vision of soldiers, improving sensitivity to harmful radiation such as UV or X-ray radiation.

The inventors have found that ceramic thin film optical detectors can be fabricated into arrays of 40 micron diameter microdetectors with 80 micron separations by microelectronics patterning and lithography methods. The microdetector size and the array geometry can be designed to meet any requirements of detector size and array geometry within the submicron limits of the microelectronic patterning and lithography technologies. Appropriate patterns can be designed for the thin film optical microdetector arrays to meet the requirements for the size and density of the photoreceptors in different positions of the retina. The thickness of the microdetectors is preferably on the order of 1 micron, with thicknesses between about 0.1 microns and about 10 microns being preferred, and thicknesses between about 0.3 microns and about 1.5 micron being particularly preferred.

The oxide-based thin film optical microdetector, which is schematically represented in FIG. 1A, is composed of a bottom electrode layer (typically platinum, although conducting oxides such as $RuSrO_3$ have been used), an optically sensitive ferroelectric oxide layer such as La doped $PbZrTiO_3$ (PLZT) and may incorporate a top thin, partially transparent conducting layer as top electrode (such as Pt or $LaSrCoO_3$). All layers are atomically ordered for maximal optical response, and are epitaxially grown by pulse laser deposition (PLD), sputtering, metallorganic chemical vapor deposition for the oxide layers, and e-beam evaporation, sputtering, or other thin film growth technique used for metal deposition for the Pt bottom electrode layer.

Figure 2A:
FIG. 2A is an SEM image of an unpatterned preferred heterostructure of this invention comprising an PLZT layer deposited on an platinum layer, which was in turn deposited on a MgO substrate.
Figure 2B:
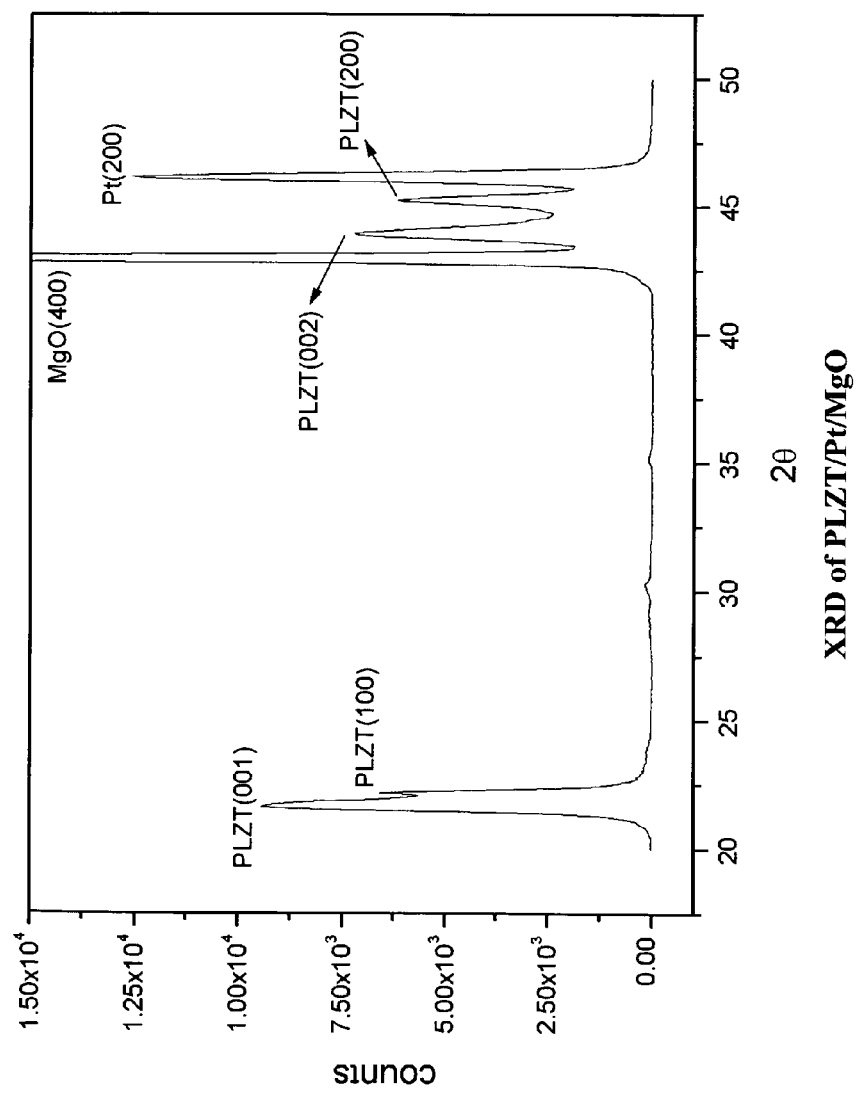
FIG. 2B is an X-ray diffraction (XRD) 2θ spectrum of a PLZT/Pt/MgO heterostructure microdetector indicating (100) atomic ordering of the PLZT active oxide layer grown on (100) ordered Pt.
Figure 2C:
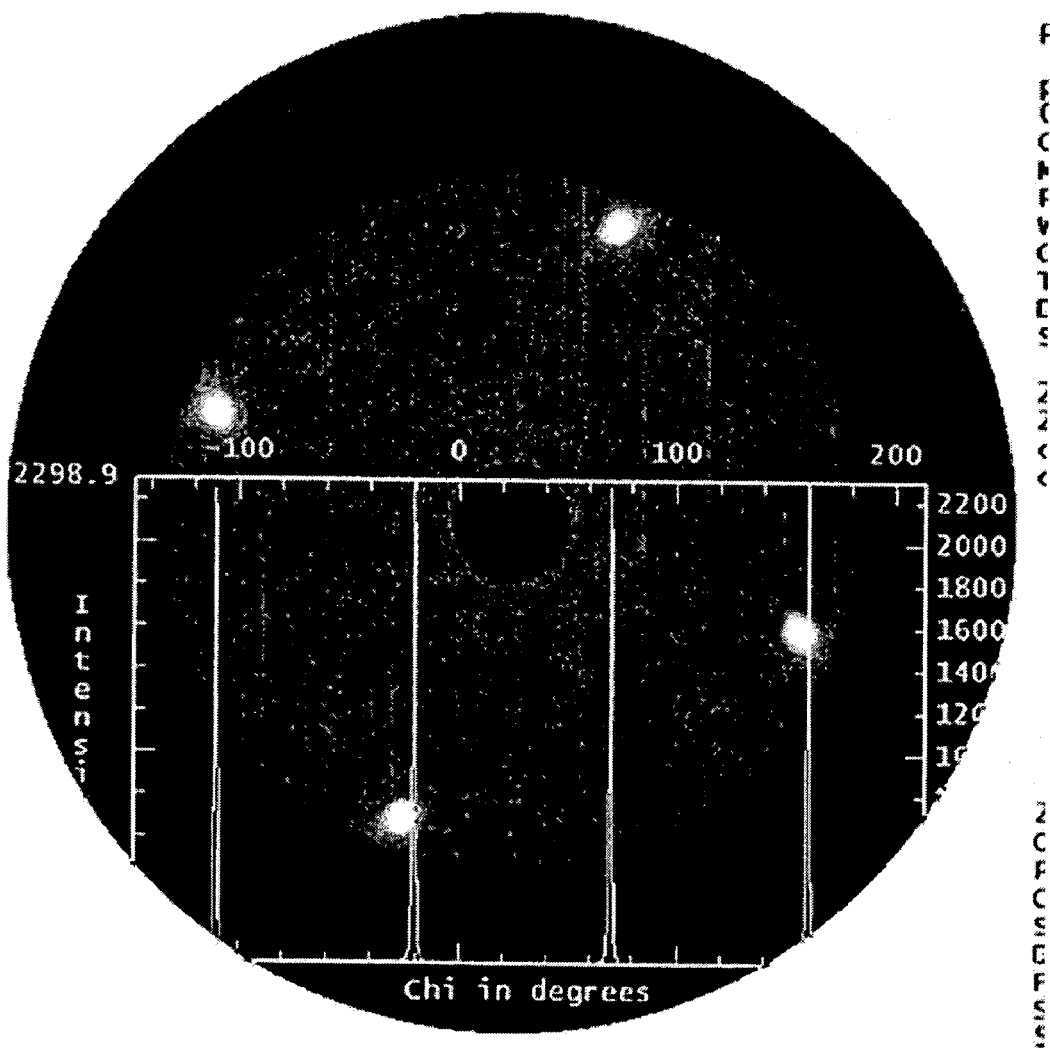
FIG. 2C is an X-ray general area detector diffraction pattern of the heterostructure of FIG. 2A having a FWHM of about 1°.
Figure 2D:
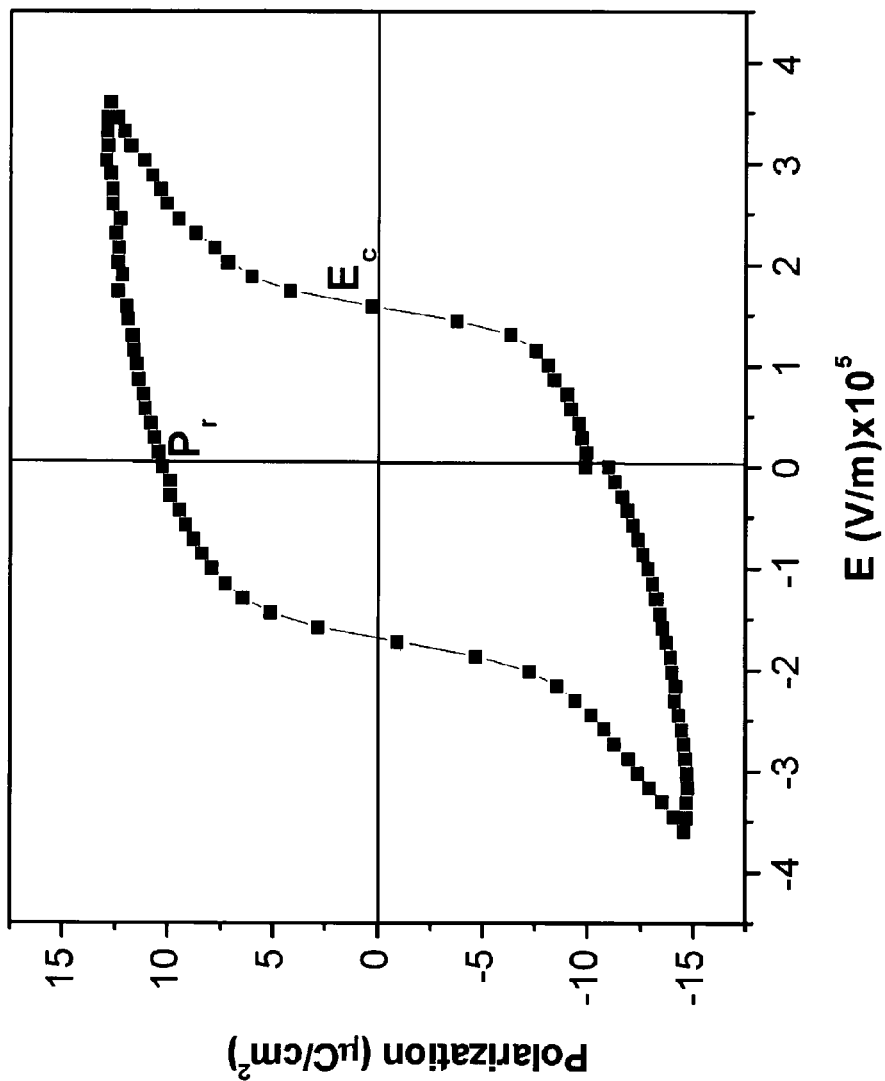
FIG. 2D is a polarization curve or hysteresis loop for the PLZT layer of the heterostructure of FIG. 2A.

In the detector fabrication process, a thin film of platinum with a thickness of 200 to 500 nm is epitaxially grown by e-beam evaporation on a single crystal MgO substrate. The PLZT layer is then grown by PLD on top of the platinum to a thickness of ~1 µm. The PLZT layer may be followed by a semi-transparent top electrode layer deposited by PLD or e-beam evaporation. The quality of the atomic order in each thin film layer is critical to optimal performance of the microdetector, and is confirmed by XRD and SEM measurements. FIG. 2B shows an XRD θ-2θ scan indicating that the PLZT grown on atomically ordered Pt is highly ordered with its (100) direction normal to the growth surface. The atomic order and thickness of the optically active ferroelectric oxide layer (e.g., PLZT) has been shown to be critical in maximizing polarization of the ferroelectric film, as shown in FIG. 2D, thus resulting in maximal photoresponse [16].

Individual microdetectors are fabricated from the PLZT/Pt/MgO heterostructure using photolithography and ion milling as is standard in the microelectronics industry. Microdetectors of 5 µm size with hexagonal packing are considered preferred designs to better mimic the size and the structure of the cone detectors in the retina.

The present invention broadly relates to optical implants including a carrier and at least one optical microdetector comprising a heterostructure including an electrical conducting layer and an optically active ceramic layer, where the ceramic layer converts light energy into electric energy sufficient to activate at least one retinal bipolar cell when the conductive layer is brought into proximity to or contact with an dendrite end of the bipolar cells.

The present invention also broadly relates to a method for making an optical implants including a carrier and at least one optical microdetector comprising a heterostructure including an electrical conducting layer and an optically active ceramic layer, where the ceramic layer converts light energy into electric energy sufficient to activate at least one retinal bipolar cell when the conductive layer is brought into proximity to or contact with an dendrite end of the bipolar cells. The method includes the steps of forming a thin film, heterostructure including a conductive layer and an optically active ceramic layer on top surface of a removable substrate, patterning the heterostructure and removing unprotected regions of the heterostructure using ion etching to form an array of optical microdetectors, and contacting the patterned heterostructure with a bio-compatible carrier.

The present invention also broadly relates to a method for implanting the implant of this invention, including the steps of making an incision into a subretinal region of a site an eye of an animal including a human, implanting the implant into the site in such as manner that the bottom conductive layer or bottom electrode of each microdetector is in electrical contact or communication with the dendrites of at least one bipolar cell in the site and allowing the incision to heal and the carrier to bio-absorb or degrade, where the implant converts light energy in to electrical energy sufficient to activate the at least one bipolar cell which in turn transmits a signal to the ganglion cells of retina and in turn to the optical nerve an eventually to the region of the brain the processes visual stimulii.

One preferred embodiment of a method of this invention for capturing optical microdetectors in an implant for improved surgical handling during implantation into an eye comprising the steps of: (1) providing an optically active thin film heterostructure on a top surface of a removable substrate; (2) forming an array comprising individual optical microdetectors from the optically active thin film heterostructure; (3) attaching a biodegradable polymer carrier membrane to the top surface of the substrate having the optical microdetector array thereon; and (4) separating the optical microdetector array attached to the biodegradable polymer carrier membrane from the soluble substrate to form an implant comprising an array of optical microdetectors in a biodegradable polymer carrier, where the implant has improved surgical handling characteristics for implantation into the eye.

Another preferred embodiment of a method of this invention for capturing optical microdetectors for improved surgical handling during implantation into an eye comprising the steps of: (1) depositing a conductive layer on a top surface of a removable substrate; (2) depositing an optically active layer on top of the conductive layer to form a thin film heterostructure of the top surface of the substrate, where the heterostructure comprises the conductive layer and the optically active layer; (3) patterning the heterostructure using negative photoresist lithography to form a patterned heterostructure; (4) removing those areas of the heterostructure not patterned during the negative photoresist lithography to form an array of optical active microdetectors on the top surface of the substrate; (5) pressing a biodegradable polymer film onto the top surface of the substrate including the optical microdetector array thereon at a temperature and pressure sufficient to secure each microdetector in the array to or in the film; and (6) removing the substrate to form an implant comprising an array of optical microdetectors in a biodegradable polymer carrier, where the implant has improved surgical handling characteristics for implantation into the eye.

Another preferred embodiment of a method of this invention for capturing optical microdetectors for improved surgical handling during implantation into an eye comprising the steps of: (1) depositing a conductive layer on a top surface of a removable substrate; (2) depositing an optically active layer on top of the conductive layer to form a thin film heterostructure of the top surface of the substrate, where the heterostructure comprises the conductive layer and the optically active layer; (3) patterning the heterostructure using positive or negative photoresist lithography to form a patterned heterostructure; (4) removing those areas of the heterostructure not patterned during the positive or negative photoresist lithography to form an array of optical active microdetectors on the top surface of the substrate; (5) forming a biodegradable polymer film onto the top surface of the substrate including the optical microdetector array thereon to secure each microdetector in the array to or in the film; and (6) removing the substrate to form an implant comprising an array of optical microdetectors in a biodegradable polymer carrier, where the implant has improved surgical handling characteristics for implantation into the eye.

Another preferred embodiment of a method of this invention for capturing optical microdetectors for improved surgical handling during implantation into an eye comprising the steps of providing an optically active thin film heterostructure on a soluble substrate; forming an array comprising individual optical microdetectors from the optically active thin film heterostructure; attaching the optical microdetector array onto a biodegradable polymer carrier membrane; and separating the optical microdetector array attached to the biodegradable polymer carrier membrane from the soluble substrate thereby capturing the optical microdetectors in the biopolymer carrier membrane for improved surgical handling of the optical micro-detectors during implantation into the eye.

Another embodiment of the present invention also relates to a method for capturing optical microdetectors for improved surgical handling during implantation into an eye comprising the steps of: (1) depositing a platinum layer on a top surface of a magnesium oxide substrate; (2) depositing a La doped $PbZrTiO_3$ layer on top of the platinum layer to form an optically active thin film heterostructure on the top surface of the substrate, where the heterostructure comprises a platinum layer and a La doped $PbZrTiO_3$ layer thereon; (3) patterning the heterostructure using positive or negative photoresist lithography to form a patterned heterostructure; (4) ion milling the patterned heterostructure to remove unprotected regions of the heterostructure to form an array of microdetectors on the top surface of the substrate, where each microdetector has a diameter of about 5 microns to about 500 microns; (5) pressing a layer of poly (dl-lactic-co-glycolic-acid) onto the optical microdetector array at a pressure of about 2000 Kg to about 2500 Kg and at a temperature of about 50° C. to about 85° C. wherein the pressed poly (dl-lactic-co-glycolic-acid) layer is less than about 500 microns thick; and (6) wet etching the magnesium oxide substrate in an about 20% by volume hydrochloric acid solution for about 24 hours to about 48 hours at room temperature; where the optical microdetector array is removed from the magnesium oxide substrate thereby capturing the optical micro-detectors in the poly (dl-lactic-co-glycolic-acid) layer for improved surgical handling of the optical micro-detectors during implantation into the eye.

In one aspect of the present invention, the optical microdetector array is formed by a heterostructure formed on a top surface of a substrate using either negative photoresist lithography or positive photoresist lithography; and removing those areas of the heterostructure not protected by the photoresist patterned during the negative photoresist lithography or patterned during the positive photoresist lithography by ion milling thereby leaving the array of optical microdetectors on the substrate. The microdetectors in the array may have diameters from about 5 microns to about 500 microns with 40 microns being a preferred size. The microdetectors can be of any convenient shape including, without limitation, circular, oval, square, rectangular, other quadrilateral shapes, pentagonal, hexagonal, heptagonal, octagonal, etc. Preferred shapes including, circular, square, and hexagonal, because these shapes allow for array configuration that mimic the distribution of cone and/or rod cells in the retina.

In another aspect of the present invention, the optical microdetector array is attached to the biodegradable membrane carrier layer by pressing a layer of the biodegradable polymer carrier membrane onto the optical microdetector array; and wet etching or dry etching the substrate under conditions wherein the optical microdetector array is removed from the substrate such that the optical microdetector array is attached to the biodegradable polymer membrane carrier layer.

In this aspect the biodegradable polymer membrane carrier layer is pressed at a pressure of from 2000 Kg to about 2500 Kg and at a temperature of about 50° C. to about 85° C. The carrier layer is less than about 500 microns thick. A representative example is from about 300 microns to about 500 microns thick. The wet etch may be performed in a hydrochloric acid solution about 20% by volume. Wet etching may be done over a period of about 24 hours to about 48 hours. The temperature was about room temperature.

Another embodiment of the present invention provides a method for capturing optical microdetectors for improved surgical handling during implantation into an eye comprising the steps of providing an optically active thin film heterostructure comprising a platinum layer and a La doped $PbZrTiO_3$ layer thereon; the platinum layer having been deposited on a magnesium oxide substrate; patterning an array onto the heterostructure using positive or negative photoresist lithography; removing those areas of the heterostructure not patterned during the positive or negative photoresist lithography by ion milling thereby leaving an array of optical micro detectors on the magnesium oxide substrate; wherein each microdetector has a diameter of about 5 microns to about 500 microns; pressing a layer of poly (dl-lactic-co-glycolic-acid) onto the optical microdetector array at a pressure of about 2000 Kg to about 2500 Kg and at a temperature of about 50° C. to about 85° C. wherein the pressed poly (dl-lactic-co-glycolic-acid) layer is less than about 500 microns thick; and wet etching the magnesium oxide substrate in an about 20% by volume hydrochloric acid solution for about 24 hours to about 48 hours at room temperature; where the optical microdetector array is removed from the magnesium oxide substrate thereby capturing the optical micro-detectors in the poly (dl-lactic-co-glycolic-acid) layer for improved surgical handling of the optical micro-detectors during implantation into the eye. The heterostructure may further comprise a top electrode. The top electrode may comprise those materials as disclosed supra.

Yet another embodiment of the present invention is directed to a method for surgically implanting optical microdetectors into an eye comprising the steps of: capturing the optical microdetectors as an array in a biodegradable polymer carrier membrane layer according to the methods as disclosed herein; implanting the biodegradable polymer carrier membrane layer containing the captured microdetector array into the eye at an implantation site; and reabsorbing the polymer carrier membrane layer such that the optical microdetectors are surgically implanted at the implantation site in a proper orientation and array configuration within the eye.

Provided herein is a method of using biodegradable polymers as temporary substrates and carrier layers for transplantation of microdetectors into the subretinal space of an eye of an animal including a human so as to substitute damaged photoreceptors in the retina with the functioning optically sensitive devices that can convert light energy into electrical energy sufficient to activate dipolar cells in the retina. Without the carrier layer support and its macroscopic size, it is almost impossible to handle the microdetectors and undertake their implantation without damage or misalignment of the devices, since the polarity of the microdetector is critical for successful operation.

The retinal prosthesis used herein is composed of oxides (ceramics) and is immune to the chemically harsh environment of the eye, thus requiring no encapsulation. The microdetector is a thin film heterostructure, which, under optical illumination, can generate a local photovoltage. The implants of this invention can be processed into microdetector arrays, from which the photovoltage will activate bipolar cells stimulating ion currents in the ganglion cells of the retina resulting in a signal at the optic nerve that may be translated by the cortex of the brain as "seeing light".

Arrays of optically active ceramic microdetectors of varying micron diameters and having a thickness of about 1 micron are integrated into a thin layer of biodegradable polymer as a carrier layer for the microdetectors. The polymer carrier layer may be any bio-compatible and biodegradable material, with poly (dl-lactic-co-glycolic-acid) (PLGA) being a preferred carrier. The fabrication of the microdetector array is possible for any size micro detector from greater than about 500 microns to less than about 5 microns and may be fabricated in any shape that is supported by photolithography and patterning techniques used in the microelectronics industry.

Although the preferred methods for making the microdetectors of this invention or the sometimes called thin film optical detectors or TODs is described above, other methods can be used as well. For example, instead to pressing a microdetector array on the MgO substrate and pressing it into a biodegradable polymer membrane, a thin film of the biodegradable polymer can be cast on top of the array or any other method for forming a biodegradable top coat on the top of the substrate having the microdetector array thereon. In an alternate method, the MgO substrate is replaced by a biodegradable polymeric substrate with the final step involving embedding the microdetectors in biodegradable polymers by cast or pressing a top membrane onto the microdetector array.

Suitable substrates for use in this invention include, without limitation, any substrate that can be removed without harm to the array or bio-polymer carrier. Preferred substrates are substrates that are soluble in a solvent or solution that does not substantially harm the array of microdetectors or the carrier onto or into which the array is carried. Exemplary examples of such substrates include magnesium oxide, potassium bromide, potassium chloride, strontium titanate, lanthanum aluminate or mixtures or combinations thereof. These exemplary examples can all be removed by contacting them is an appropriate solvent or solution such as water, acidic water, basic water or the like.

Suitable heterostructures for use in this invention comprise a bottom electrode or conductive layer, an optically active layer and, optionally, a top electrode or conductive layer. Suitable material for use as the bottom electrode or conductive layer include, without limitation, any conductive material having sufficient biostability. Exemplary examples of material suitable for the bottom electrode are platinum, gold, a conducting oxide such as $LaSrCoO_3$ $RuO_2$, or $IrO_2$ doped $CeO_2$ or other conducting oxide or mixtures or combinations thereof. Suitable material for use as the optically active layer include, without limitation, an oxide or a nitride or mixture or combinations thereof. Exemplary examples of material suitable are ZnO, BiVMgO, GaN, BN, and a doped perovskite, where the dopant includes, without limitation La, Nb, Sb, Mn, Ca or mixtures or combinations thereof. Suitable material for use as the top electrode or conductive layer include, without limitation, any conductive material having sufficient biostability. Exemplary examples of material suitable for the top electrode are platinum, gold, $LaSrCoO_3$, $RuO_2$, $IrO_2$ doped $CeO_2$, or other conducting oxide or mixture or combinations thereof.

The term sufficient biostability means that the material does not decompose in the body during an extended period of time and does not illicit a significant immune response. The extended period of time should be at least 10 years and preferably for the life of the animal or human into which the implant is implanted. The term significant immune response means a response which would necessitate removal of the implant. The term biodegradable or bioerodible or bioabsorbable means that the bio-polymers substantially or completely dissolves over a period of time when exposed to aqueous environments including biological fluids found in animal or human bodies.

Suitable bio-polymers for use in the present invention include, without limitation, biocompatible polymers that are preferably bioerodible by cellular action and/or are biodegradable by action of non-living body fluid components. Such polymeric substances include polyesters, polyamides, polypeptides and/or polysaccharides or the like.

Non-limiting examples of suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof. The preferred biodegradable polymers are all degraded by hydrolysis.

Typically, the polymers will either be surface erodible polymers such as polyanhydrides or bulk erodible polymers such as polyorthoesters. Poly(l-lactic acid) (PlLA), poly(dl-lactic acid) (PLA), poly(glycolic acid) (PGA), poly(l-glycolic acid) (PlGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLGA). The co-monomer (lactide:glycolide) ratios of the poly(dl-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(dl-lactic-co-glycolic acid) offer the advantage of a large spectrum of degradation rates from a few days to years by simply varying the copolymer ratio of lactic acid to glycolic acid. Representative examples of the biodegradable polymer are polyglycolic acid, poly-l-lactide, poly-dl-lactide, caprolactane, dl-lactic-co-glycolic-acid or other co-polymers thereof.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration. Additionally, the bio-polymer can include a buffering agent to ensure that the pH of the surrounding tissue remains near its normal pH during biodegradation. By near its normal pH, the inventors mean that the pH is within about 1.5 pH units of the normal pH of the surrounding tissue, preferably, within about 1 pH unit and particularly, within about 0.5 pH units of the normal pH of the surrounding tissue.

The implants of this invention comprising arrays of thin film oxide optical microdetectors and their implantation technology represent a ideal approach to correcting or restoring vision in term of simplicity, durability, biocompatibility and implantation mechanism. In addition, the micro size of the microdetectors, generated by microelectronics-based photolithography and patterning assures size compatibility with human detectors as well as arrangements of the detectors in arrays mimicking human retinal detector densities and configurations. Finally, the method of transfer and implantation of detectors using a solvable polymer carrier layer supporting a microdetector array that is inserted into the post retinal space, allows for the direct replacement of damaged photoreceptors in the retina of a retinally blind patient. Biocompatibility tests have shown positive response for the oxide thin film detectors, and laboratory-measured photovoltage output has been shown an electric potential, and resultant electric field believed to be adequate enough to excite the ocular neural network. Such microdetectors have the promise of restoration of sight to retinally blind people and in maintaining sight in people with eye disease that do not destroy the bipolar cells of the retina.

The following examples are given for the purpose of illustrating various embodiments of the invention and are not meant to limit the present invention in any fashion.

EXAMPLE 1

This example illustrates the fabrication of an optically active thin film heterostructure of this invention.

Figure 1B:
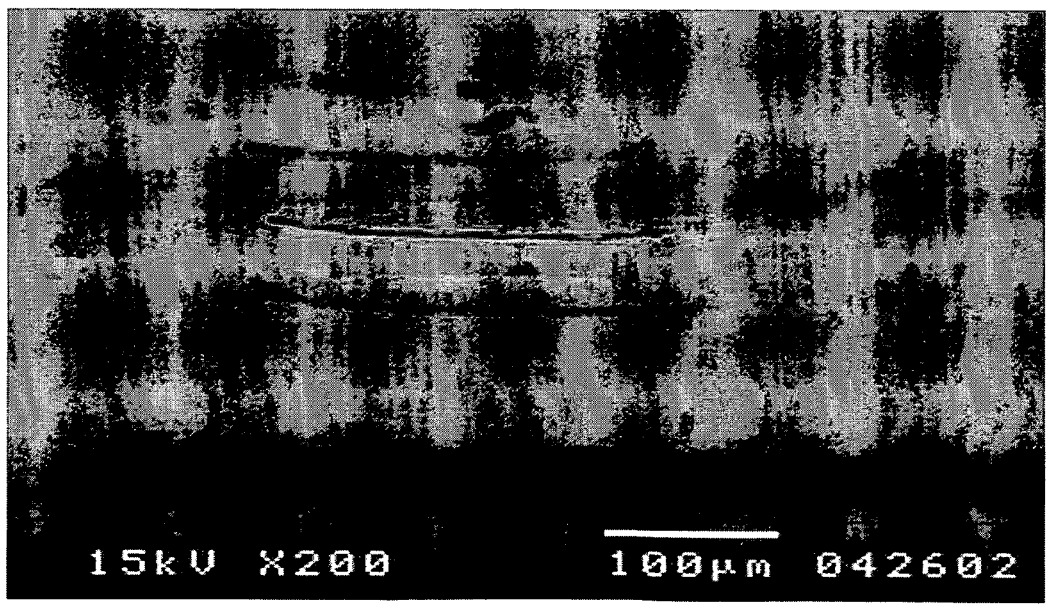
FIG. 1B is an SEM image of several thin film microdetectors on a MgO substrate.

A ceramic-based, thin film optical microdetectors of this invention is represented schematically in FIG. 1A. The microdetector 100 is composed of biologically inert materials and includes a bottom electrode layer 102, where the layer is platinum, gold, or a conducting oxide such as $LaSrCoO_3$, $RuO_2$, doped $CeO_2$, or $IrO_2$ or mixtures thereof, an optically sensitive oxide layer 104 such as La doped $PbZrTiO_3$ (PLZT) or other optically active perovskite. It is further contemplated that other doping elements for $PbZrTiO_3$, including Sb, Mn, and Ca, can be used. Additionally, optically active oxides or nitrides such as ZnO, BiVMgO (BVM), GaN, or BN can be used. Optionally, the optical detector 100 may optionally include a top partially transparent conducting layer 106 as top electrode, where the this conductive layer is Pt, Au, $LaSrCoO_3$ or other conducting oxide or mixtures thereof. Looking at FIG. 1B, a SEM microgram of several microdetectors 100 are shown on a MgO substrate 108.

All layers are atomically ordered for maximal optical response, although layers with limited atomic ordering can be used with reduced optical response. The layers are epitaxially grown into the thin film heterostructure by any technique for oxide thin film growth including pulse laser deposition (PLD), organometallic chemical vapor deposition (OM-CVD), rf-sputtering or e-beam evaporation.

In the detector fabrication process, the bottom conductive layer 102 comprises, in this embodiment, a thin film of platinum having a thickness $d_1$ between about 50 nm and about 500 nm is epitaxially grown by e-beam evaporation on a single crystal MgO substrate or other deposition-stable and water-soluble substrate, e.g., potassium bromide, potassium chloride, or other material. The PLZT layer 104 is then grown by pulse laser deposition on top of the platinum layer 102 to a thickness of about 1 micron. Optionally, a top electrode layer 106 may be deposited by pulse laser deposition or e-beam evaporation onto the PLZT layer 104.

The atomic quality of the thin film in each layer is critical to optimal performance and is confirmed by XRD and SEM measurements. The atomic ordering of the heterostructure layers is critical in maximizing polarization of the ferroelectric film, thus resulting in maximal photoferroelectric response. Looking at FIG. 2A, a SEM of the PLZT layer 104 is shown which is on top of the bottom conductive layer 102 (not shown), which is in turn on a MgO substrate (not shown). Looking a FIG. 2B, an XRD spectrum is shown of two layers 102 and 104 showing a single peak for the single crystal MgO substrate, a single peak for the atomically ordered Pt conductive layer 102 grown on the MgO, and a set of (001)-type peaks for the PLZT layer 104 indicating atomic order of the PLZT in the direction normal to the surface of the PLZT layer. Looking at FIG. 2C, an X-ray general area detector diffraction pattern of the PLZT layer 104 is shown to include four bright spots indicating atomic order in the plane of the PLZT layer. FIGS. 2B and 2C jointly indicate essentially a single crystalline form of the PLZT in the layer 104. Looking at FIG. 2D, a polarization curve for the PLZT layer 104 is shown indicating strong ferroelectric properties of the PLZT layer.

Figure 3A:
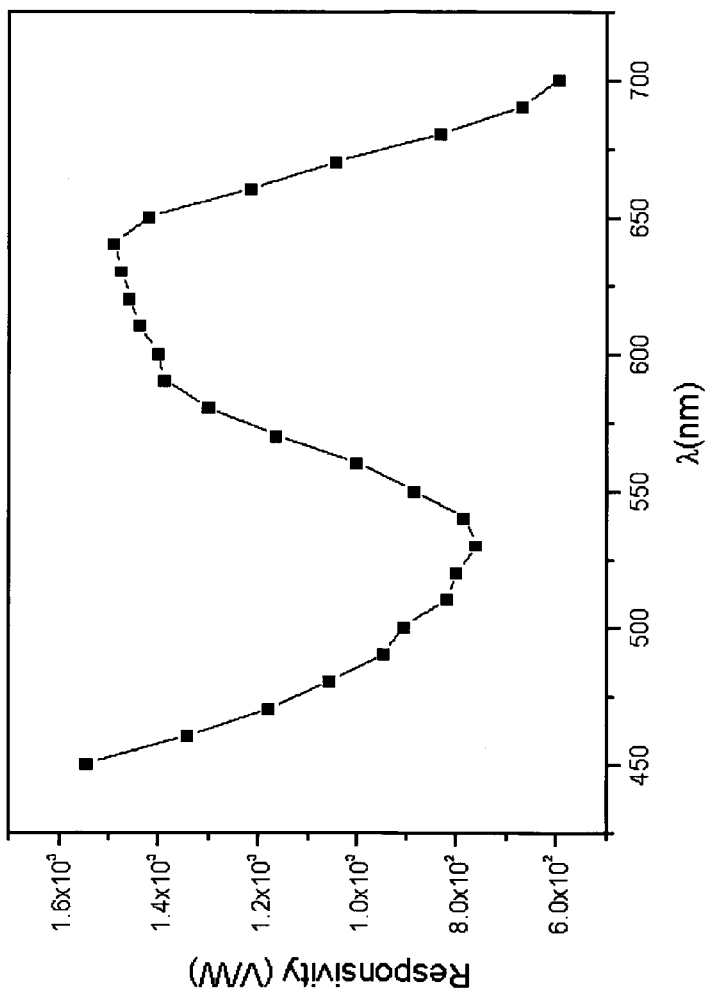
FIG. 3A is an absorption spectrum of a lanthanum doped $PbZrTiO_3$ (PLZT) thin film having the composition $PbZr_{0.52}Ti_{0.48}O_3$ showing absorptions in the visible part of the spectrum.

The spectral response of the thin film oxide micro-detector is governed by the optical properties of the active ferroelectric oxide layer of the heterostructure. A ferroelectric oxide film with a spectral sensitivity close to that of the human eye is best to use for the detector. A number of oxide films have been investigated as to optical response, and as an example lanthanum doped $PbZrTiO_3$ (PLZT) is shown to have a spectral response that overlaps human eye response. The photo-voltage spectral response of the detector measured by a xenon discharge lamp integrated with a monochrometer indicates that the PLZT detector has a peak in its optical response in the visible range at ~550 nm with sensitivity extending out to nearly 700 nm as is seen in FIG. 3A.

Figure 3B:
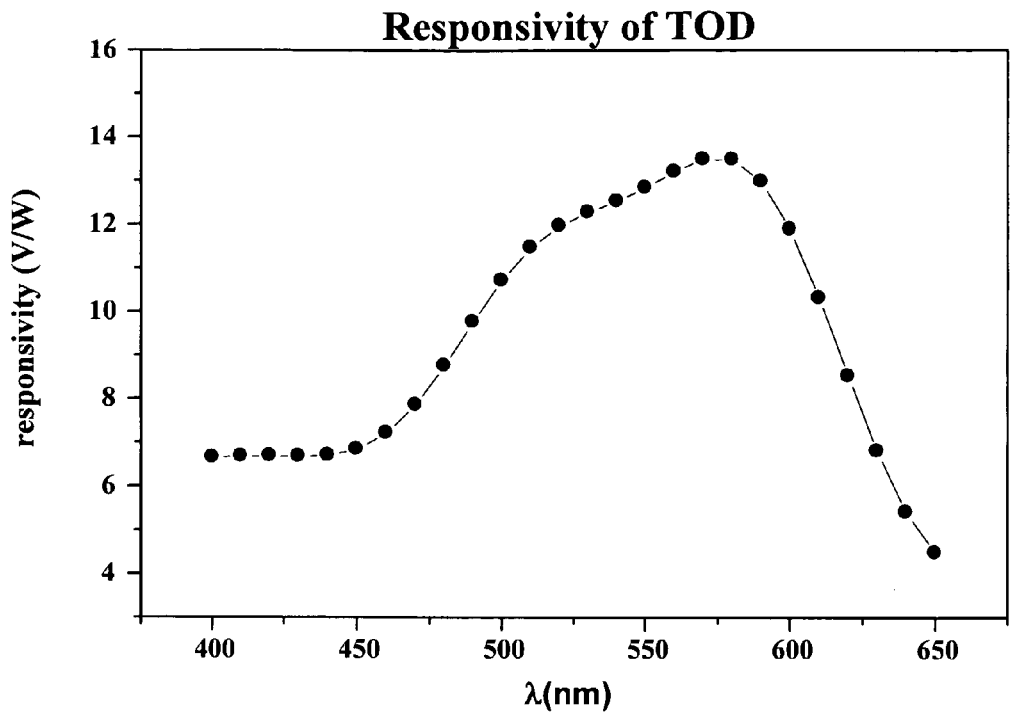
FIG. 3B is an absorption spectrum of an TOD of this invention fabricated from the thin film of FIG. 3A showing absorptions in the visible part of the spectrum.
Figure 3C:
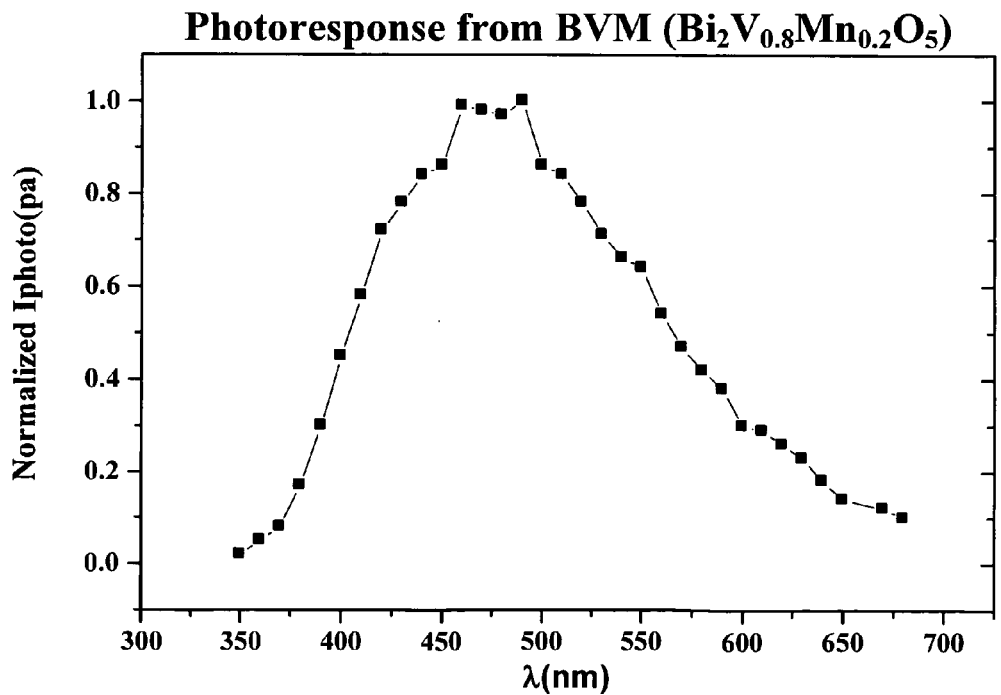
FIG. 3C is an absorption spectrum of a $Bi_2V_{0.8}Mn_{0.2}O_5$ (BVM) thin film showing absorptions in the visible part of the spectrum.
Figure 3D:
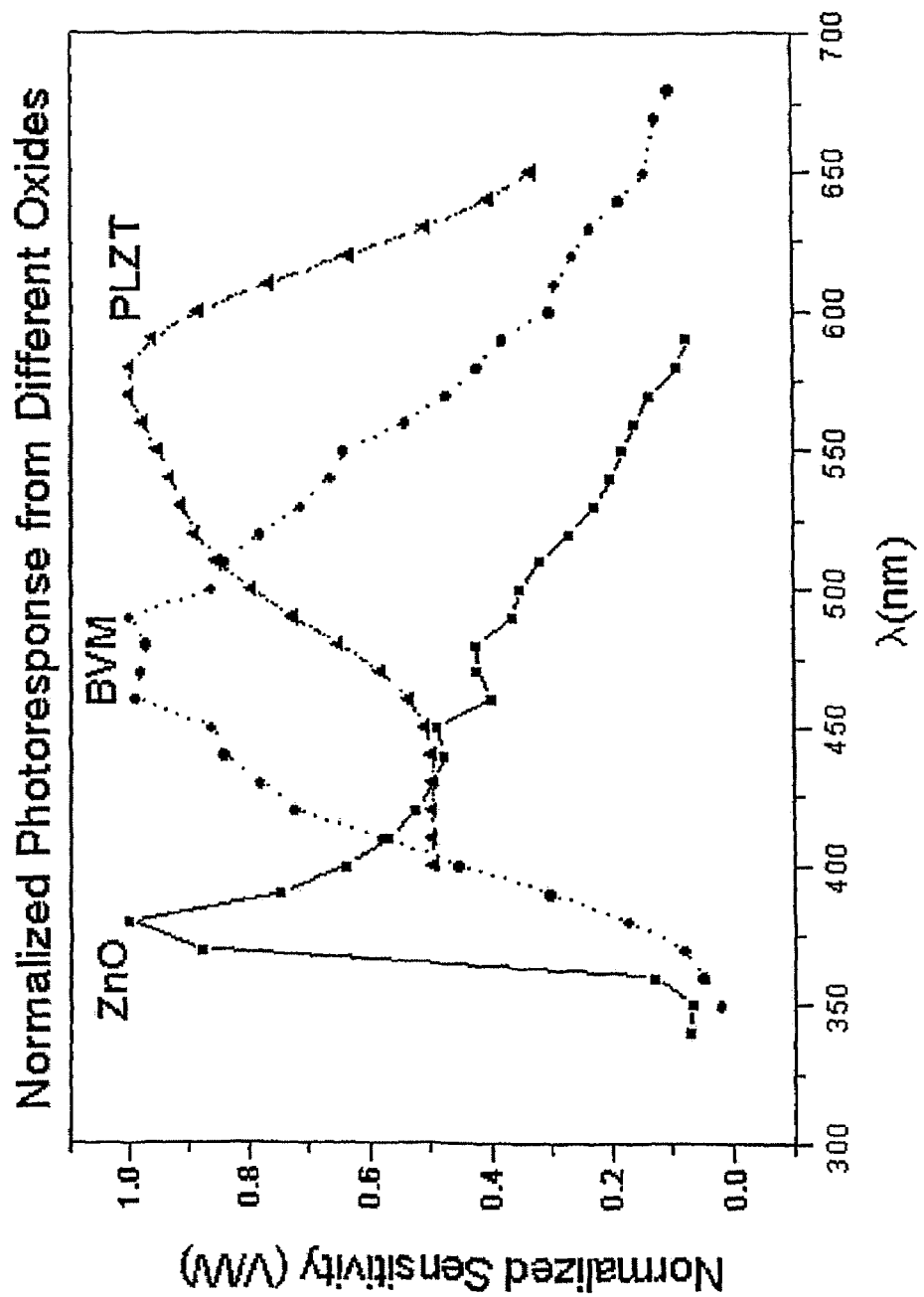
FIG. 3D is an absorption spectra depicting the spectral responses of several different oxide thin films showing absorptions in the visible part of the spectrum for construction of microdetectors with red, green and blue spectral responses.

The device is then tested for optical response, using a xenon discharge lamp and monochrometer with a spectral output from 350-700 nm. Looking at FIG. 3A, an optical response curve for the PLZT layer 104 is shown, evidencing a strong response in 450 nm wavelength region of the electromagnetic spectrum and in the 575 nm to 650 nm region of the electromagnetic spectrum. Looking at FIG. 3B, an optical response curve for a TOD of this invention is shown and can be seen as having a slight different strong response region, which is between about 500 nm and about 600 nm. Looking at FIG. 3C, an optical response curve for a BVM material is shown, which has a response in the wavelength region between about 400 nm and about 550 nm. Looking at FIG. 3D, a normalized optical response of ZnO, BVM and PLZT oxide thin films over the visible spectrum is shown. Each oxide thin film exhibits a response in the visible region, but each has a peak in response at a slightly different wavelength. Thus, arrays of mixed oxide material detectors would provide for color sensitivity across, by providing red, green and blue microdetectors made of different oxides, with red microdetectors preferably base on PLZT, with green microdetectors preferably based on BVM and with blue microdetectors preferably based on ZnO. However, other red, green or blue light sensitive oxides may be even more preferred.

EXAMPLE 2

This example illustrates the fabrication of individual optical devices from heterostructure of this invention.

Figure 4:
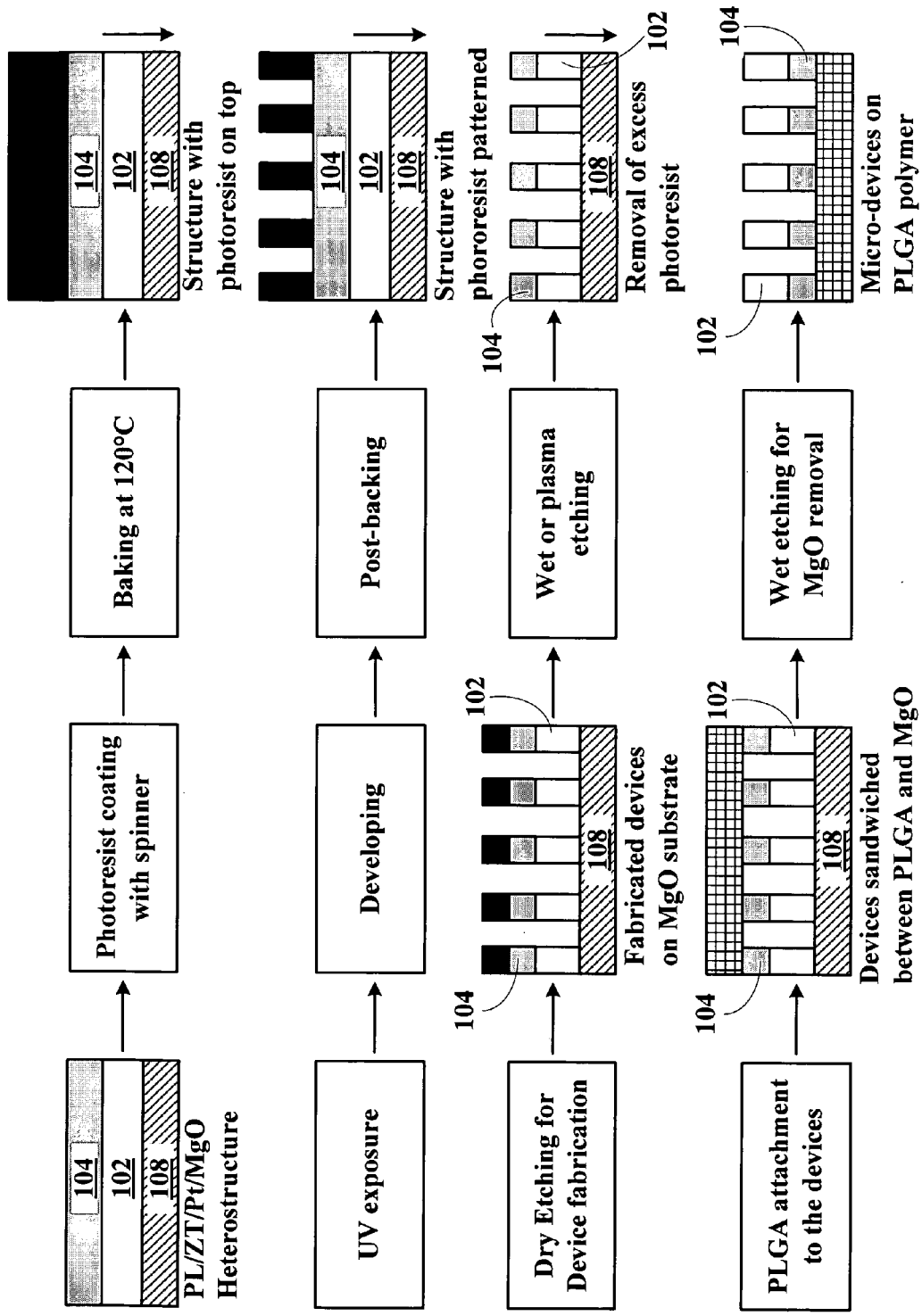
FIG. 4 a schematic of the patterning and transfer process of the microdetectors to the polymer membrane.

Individual microdetectors or arrays of microdetectors are fabricated from the resultant heterostructure using negative photoresist lithography and ion milling as is standard in the microelectronics industry. The fabrication process is shown schematically in FIG. 4. In FIG. 4, the optically active heterostructure include a conductive layer 102 and a ceramic layer 104 on a substrate 108. Next, the heterostructure is covered by a uniform layer of negative photoresist by means of a spinner and baked on at 120° C. The micro-detector array is then patterned on the photoresist by using an appropriate pattern mask, e.g., an array of 40 micron diameter dots with 80 micron spacing, and the photoresist is exposed to UV light. The photoresist is then developed revealing a pattern of 40 micron dots of photoresist left at the surface of the heterostructure. The PLZT/Pt not covered with photoresist is then removed by ion milling and excess photoresist is removed by wet etching or plasma etching, thus leaving an array of devices on the MgO substrate. Microdetectors made in this process range from large sizes of 500 microns for the ease of individual handling to smaller sizes of 5 microns. This technique can be used to make microdetectors of 5 micron in size with hexagonal packing or other packings to better mimic the size and the structure of the cones and/or rods in the retina. A positive photoresist photolithographic process also can be used. With a positive photoresist the patterned areas are removed, hence, the space between the microdetectors is patterned and then removed.

EXAMPLE 3

This example illustrates attaching the polymer membrane to an optical array of this invention.

Figure 5A:
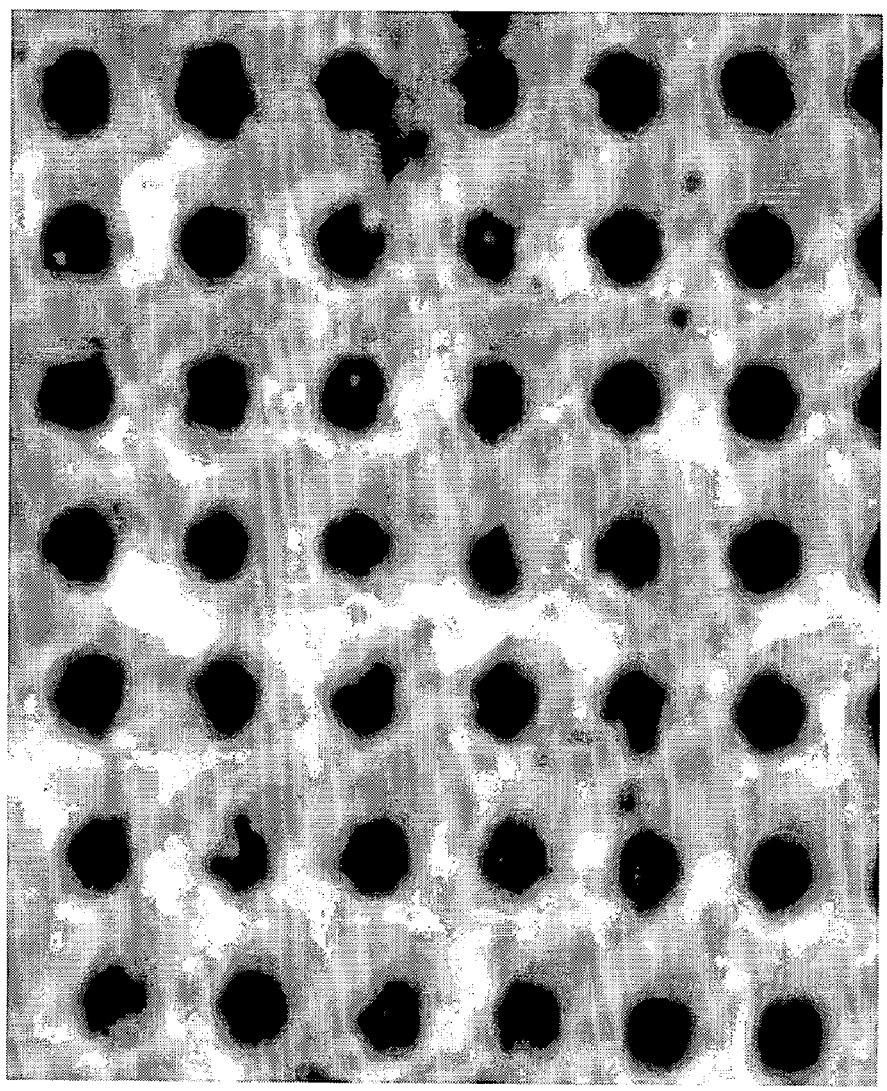
FIG. 5A depicts a micrograph of an array of 80 micron diameter PLZT-based TOD devices with 160 micron spacing mounted on PLGA polymer carrier film.
Figure 5B:
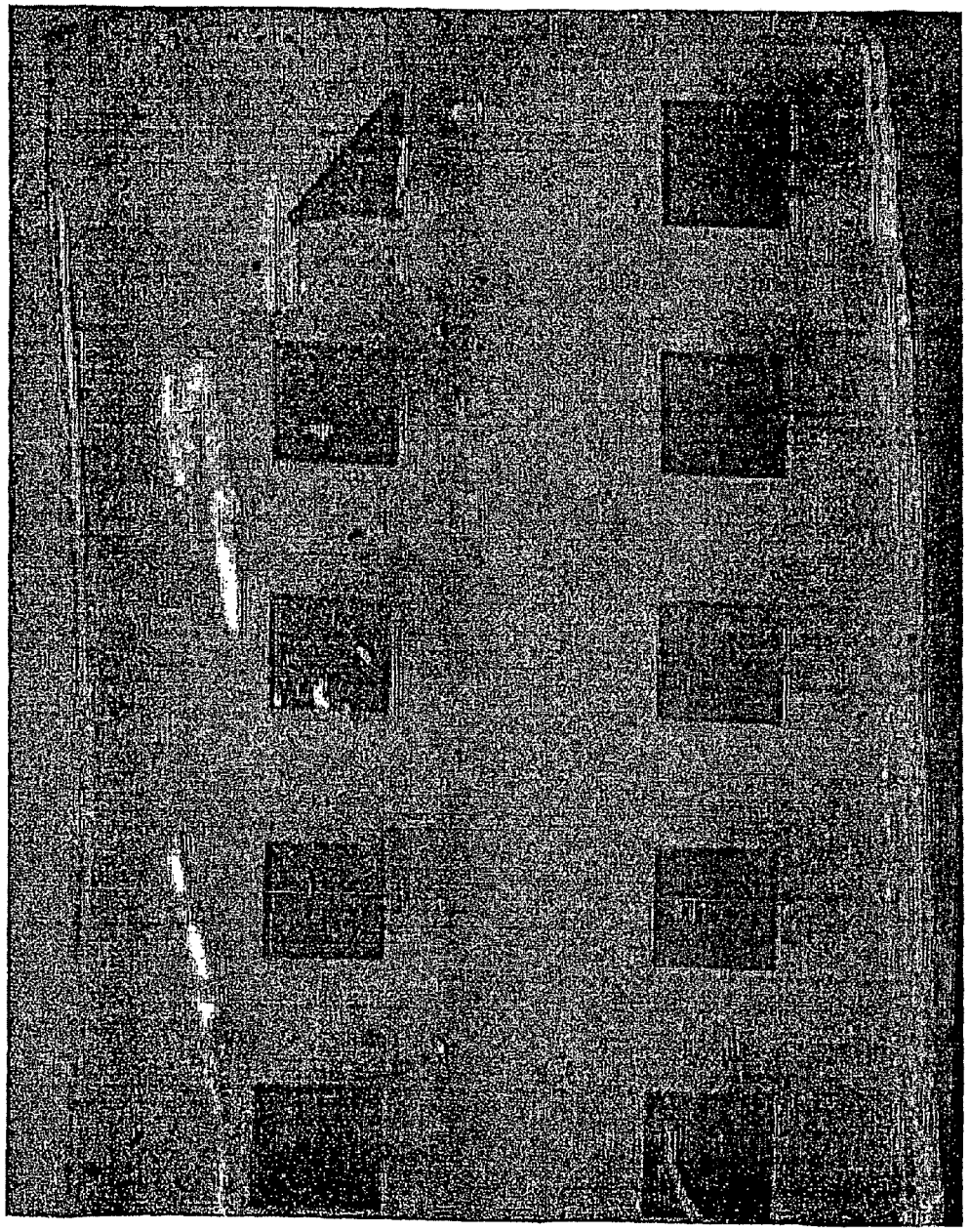
FIG. 5B depicts a micrograph of an array of 200 micron square PLZT-based TOD devices mounted on PLGA polymer carrier film.
Figure 5D:
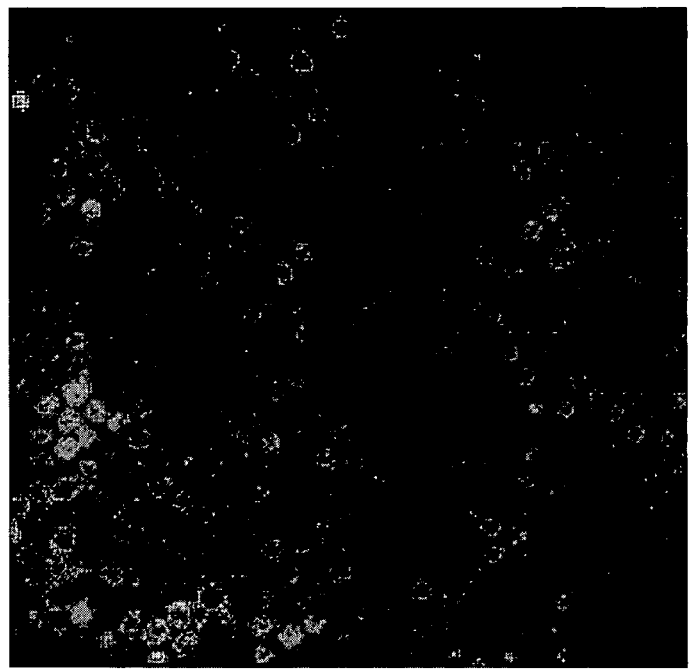
FIG. 5D is picture of the cones and rods in the retina, where the light grey cells are green sensitive cones, the darker grey are red sensitive cones and the dark grey are blue sensitive cones.
Figure 5C:
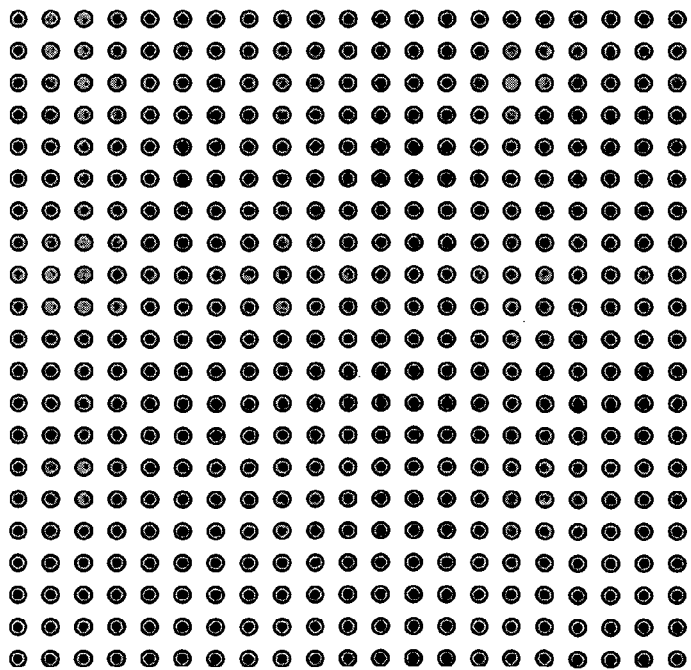
FIG. 5C is a preferred pattern of microdetectors of this invention to mimic the distribution of cones and/or rods in the retina of an eye.
Figure 5E:
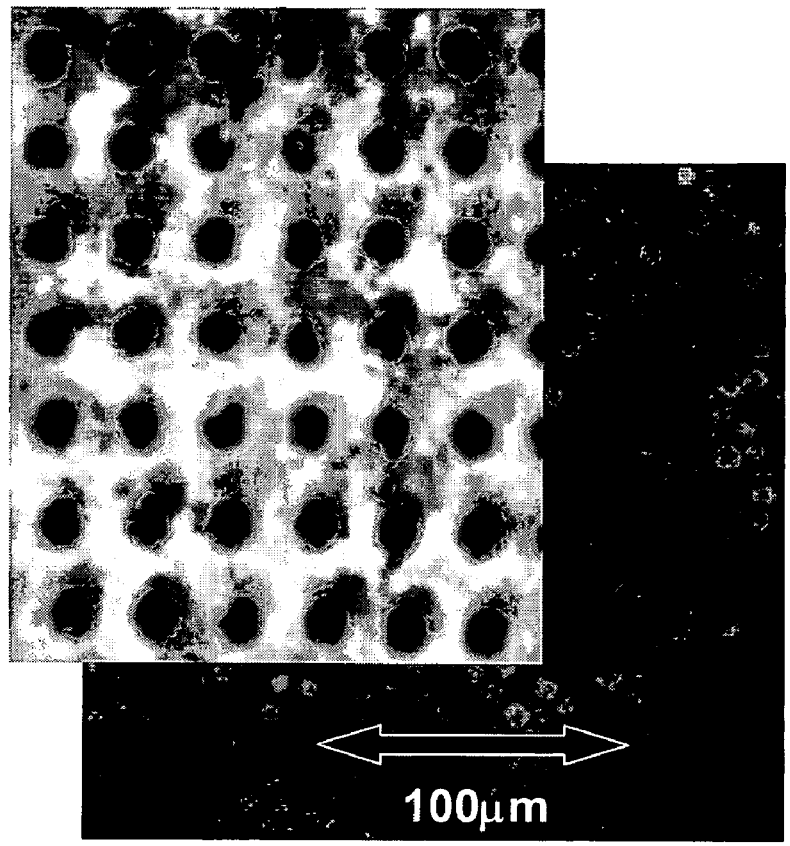
FIG. 5E is a composite picture showing an array of microdetectors of this invention on a biodegradable PLGA membrane patterned to mimic the pattern of cones in the retina shown below, where the scale is on the order of 100 microns.
Figure 6A:
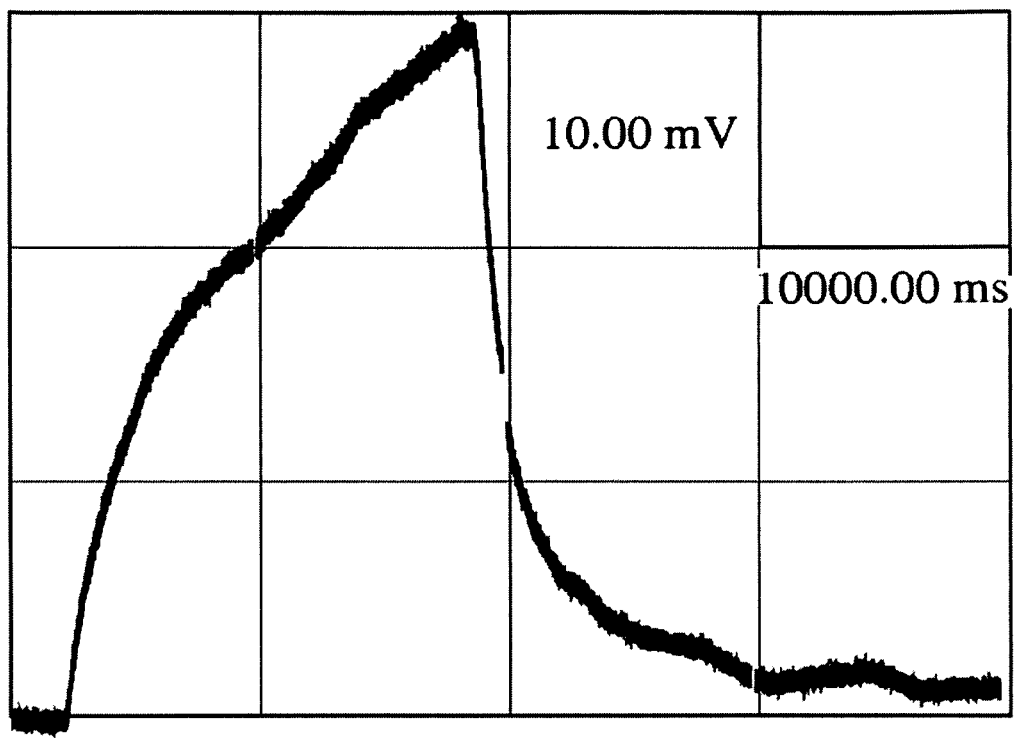
FIG. 6A is a spectrum of the output of the TOD having a thickness of about 250 microns illuminated with a light intensity of about 1 $mW/cm^2$.
Figure 6B:
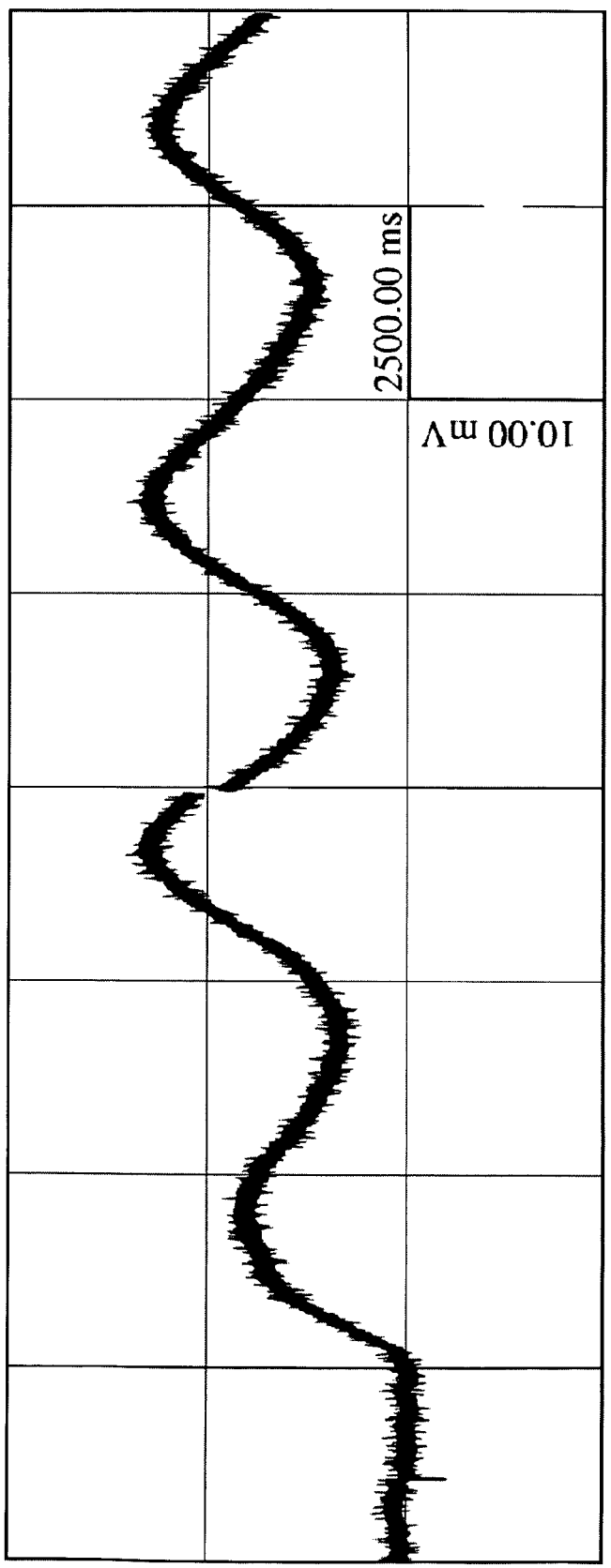
FIG. 6B is a spectrum of the output of the TOD having a thickness of about 250 microns illuminated with a variable intensity light source where the intensity is about 1 $mW/cm^2$.
Figure 6C:
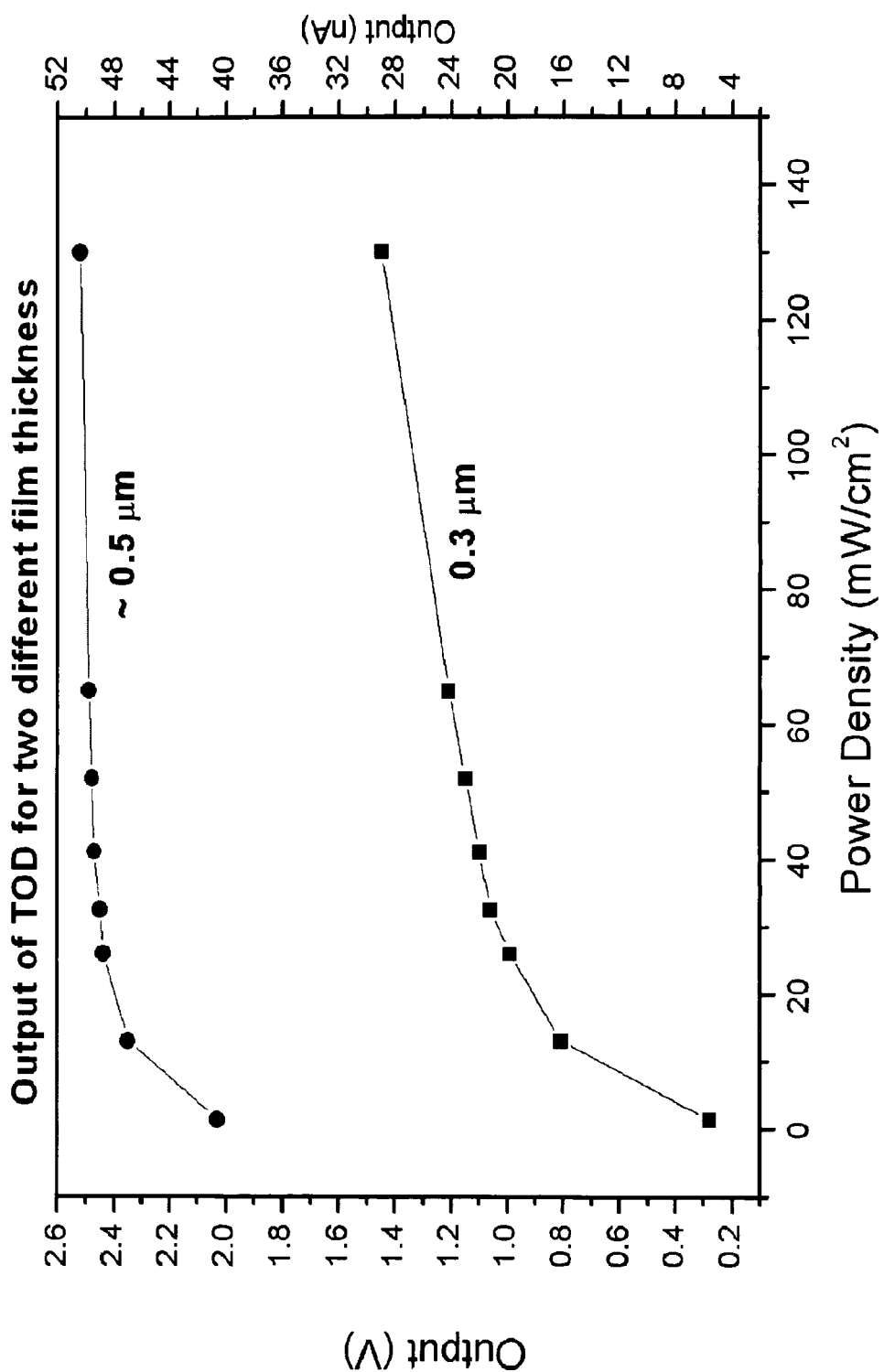
FIG. 6C is a plot of TOD output (V) verses power density of light ($mW/cm^2$) for the TOD having two different TOD thicknesses: about 0.5 microns and about 0.3 microns.
Figure 6D:
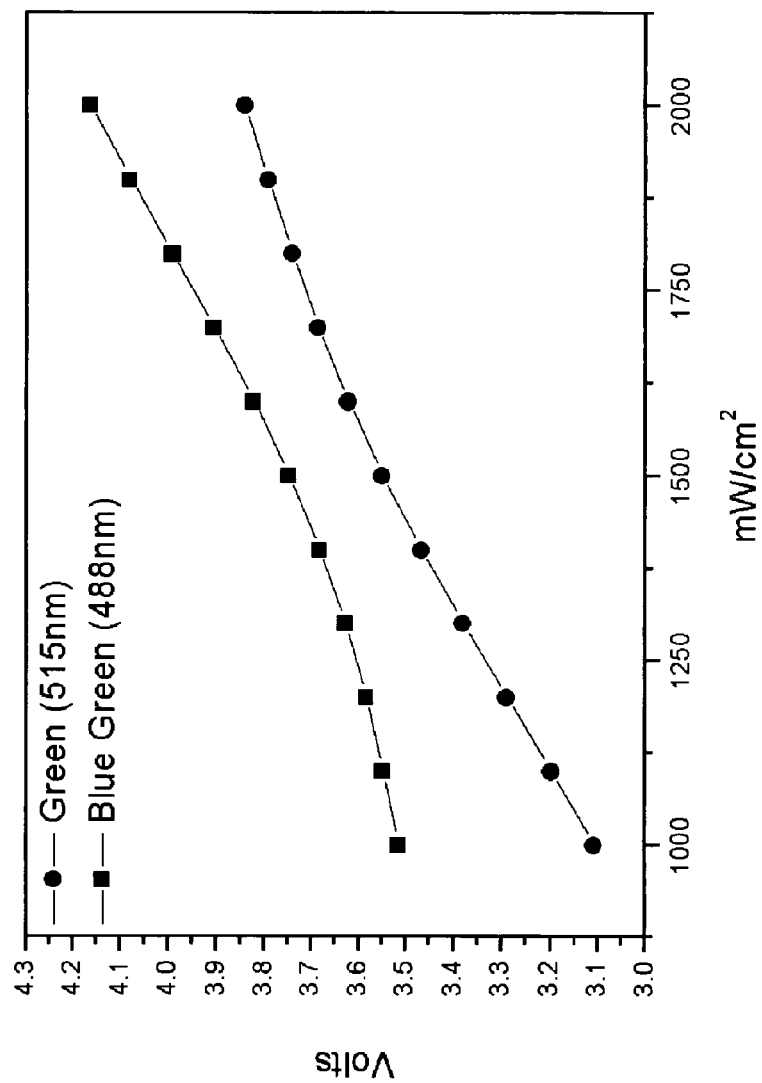
FIG. 6D is a plot of TOD output (V) verses power density of light ($mW/cm^2$) for the TOD of having two different wave length of light: Green 515 nm and Blue Green 488 nm.

After the detector arrays are photolithographically patterned on the MgO substrate, the polymer membrane is pressed onto the microdetectors for attachment to the membrane. Wet etching of the MgO substrate is then performed to remove the micro-detector array from the substrate, but leave the polymer carrier layer intact. The wet etching for an MgO substrate is performed in a ~20% volume concentration of HCl for a period of 24 to 48 hours at room temperature. A dry etch process may also be performed to remove the substrate. This leaves the microdetectors attached to the polymer in their proper array, and with correct orientation and lateral placement for implant into the eye. FIG. 5A shows a TOD device with an 80 micron diameter microdetector and 160 micron spacing mounted on a PLGA polymer film used as a carrier and FIG. 5B shows a TOD device with a 200 micron square microdetector array. FIG. 5C shows a preferred TOD array, which is designed to mimic the distribution of cones in the retina as shown in FIG. 5D. FIG. 5E shows a microgram of a fabricated array having the preferred distribution overlaid on a portion of the retina showing the cones.

The polymer membrane carrier layer in this example is PLGA polymer (dl-lactic-co-glycolic acid) which was shown to be tissue compatible, and is reabsorbed by the body over a period of days or weeks degrading on composition and thickness. The membrane layer is made by pressing the PLGA powder into about a 300 micron thick layer pressures from about 2000 Kg to about 2500 Kg at about 50° C. to about 85° C. The 300 micron membrane is easily handled and has a short dissolution time, i.e., several days.

EXAMPLE 4

This example illustrates the schematic implantation of a microdector array of this invention into a retina.

Figure 7A:
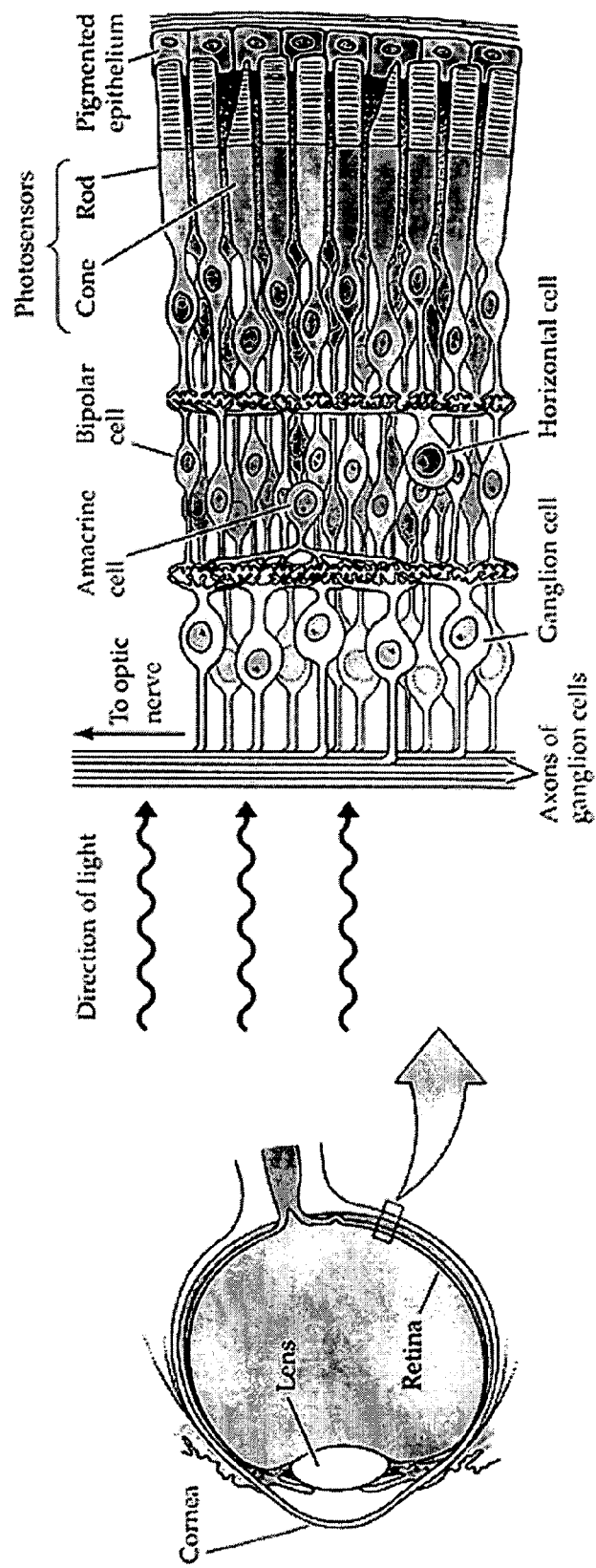
FIG. 7A is a schematic depiction of a segment of the retina of an eye showing the different layers of cells in the retina relative to light radiation, waving lines, which impinges on the retina.
Figure 7B:
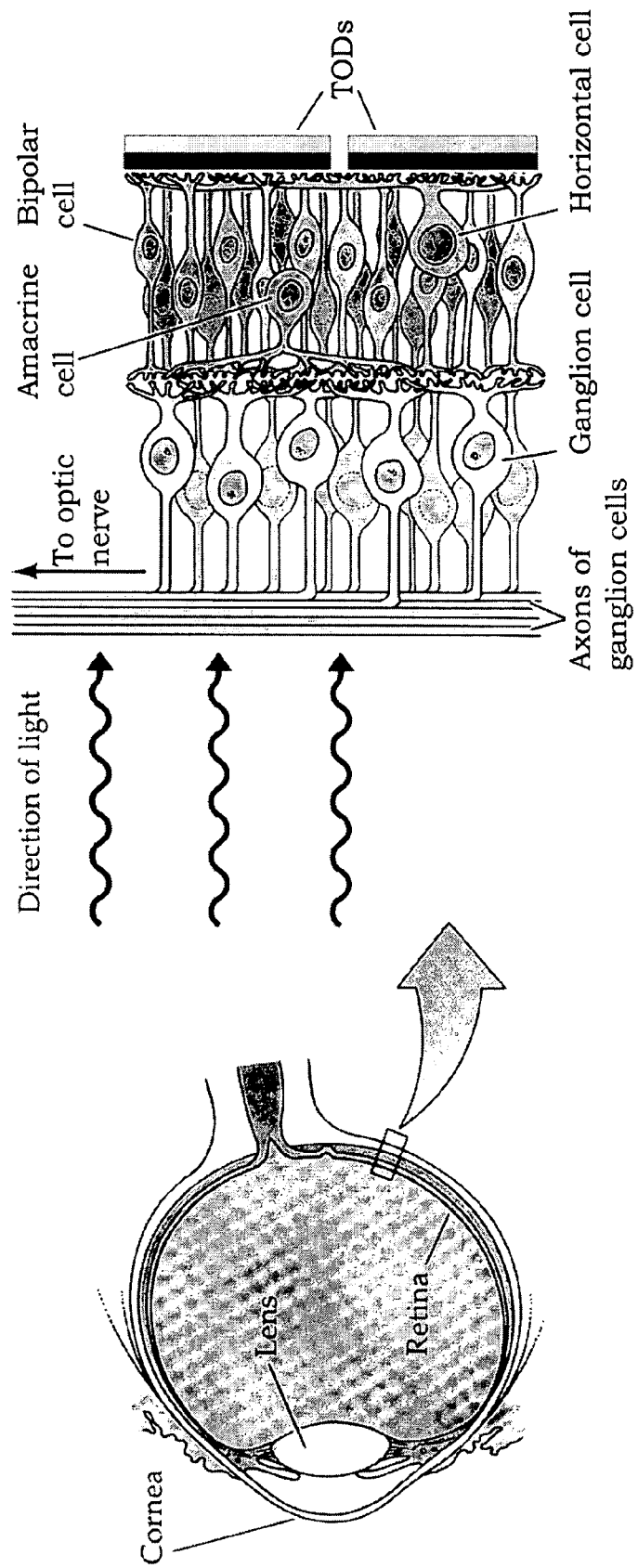
FIG. 7B is a schematic depiction of a segment of the retina of an eye showing the different layers of cells in the retina with the TOD implant of this invention replacing the rods and cones cell layer in the same orientation as the retinal section of FIG. 7A.
Figure 7C:
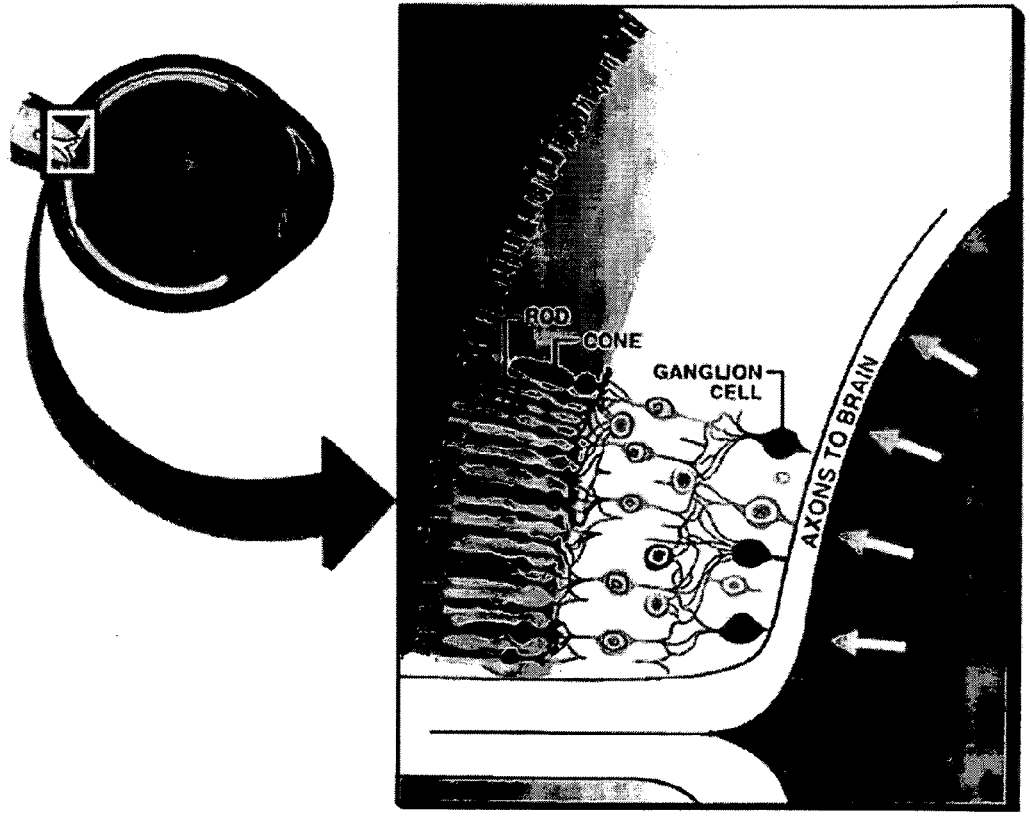
FIG. 7C depicts is another schematic depiction of a segment of the retina of an eye showing the different layers of cells in the retina with an implant of this invention including an array of TODs, where the implant replaces the rods and cones cell layer in a section of the retina.

Referring now to FIG. 7A, pictorial depiction of a section 200 of a retina 202 from an eye 204. The retina 202 includes an axon of ganglion cell layer 206, a ganglion cell layer 208, an amacrine cell and bipolar cell layer 210 and an contact layer 212 interposed therebetween, a photoreceptor layer 214 comprising cone and rod cells, a contact layer 216 interposed therebetween and a pigmented epithelium layer 218. FIG. 7B is a pictorial depiction of a section 200 of a retina 202 from an eye 204. The retina 202 includes an axon of ganglion cell layer 206, a ganglion cell layer 208, an amacrine cell and bipolar cell layer 210 and an contact layer 212 interposed therebetween, a TOD 220, and a contact layer 216 interposed therebetween.

For blind subjects with photoreceptor degeneration, subretinal implantation of the TOD array, which is the proper physiological position for photoreceptors, is the most appropriate approach for the following reasons: it directly replaces damaged rods and cones with the TODs of similar or equal size and configuration, and it couples the detectors directly to the intact retinal bipolar and horizontal cells without needs for additional wire interconnections. This simplicity of design promises both exceptional functionality and ease of implantation for the ceramic microdetectors.

The TOD optical response data above indicates that under nominal lighting conditions, the output of TOD is several 10's of mV. Local action potentials required for ganglion cell function and resultant sensation of "seeing" are of this magnitude [18]. Hence it is highly likely that the implanted TOD's will generate sufficient local photovoltage and resultant high local electric field to activate the neighboring bipolar cells. It should be noted that since the photovoltaic characteristics of the TOD increase with thickness of the active oxide layer in the device [4], fabricating devices with thicker active layer can also enhance the voltage output of the TOD's if needed.

The above described ceramic microdetectors utilize visible light as both the stimulus and the power source, with an electrical output characteristic appropriate to stimulate bipolar and horizontal cells. The structure and placement of the microdetectors allows for their signals to be directly integrated into the existing intact neural circuitry of the eye so as to get signals to the brain. The TOD's also have a small individual size, and can be patterned to any size even that approaching the size of natural cone receptors, thus allowing for the possibility of sight resolution as well as allowing for nutrient flow through the detector array to the interior of the eye.

This invention defines a plurality of thin film oxide microdetectors mounted on a biodegradable carrier that can be implanted into the subretina space and become integrated into the retina replacing the cone and rod cells. The implants of this invention comprising arrays of thin film oxide optical microdetectors and their handling though a developed biodegradable polymer carrier layer technology, represent an ideal approach to correcting or restoring vision in term of simplicity, durability, biocompatibility and implantation mechanism. In addition, the micro size of the microdetectors, generated by microelectronics-based photolithography and patterning assures size compatibility with human detectors as well as arrangements of the detectors in arrays mimicking human retinal detector densities and configurations. Finally, the method of handling and transfer of the microdetectors using a solvable polymer carrier layer supporting a microdetector array that is inserted into the post retinal space, allows for the direct replacement of damaged photoreceptors in the retina of a retinally blind patient. Laboratory-measured photovoltage response has been shown the generation of an electric potential and concomitant electric field believed to be adequate enough to excite the ocular neural network. Such microdetectors have the promise of restoration of sight to retinally blind people.

REFERENCES

1. M. S. Humayun, R. Propst, E. de Juan, D. McCormick and D. Hickingbotham. Bipolar surface electrical stimulation of the vertebrate retina. Arch. Ophthalmol., Vol. 112, pgs. 110-116 (1994).

2. M. S. Humayun, E. de Juan, G. Dannelie, R. J. Greenberg, R. H. Probst and H. Phillips. Visual perception elicited by electrical simulation of retina in blind humans. Arch. Opthalmol. Vol. 114, pgs. 40-46 (1996).

3. A. Y. Chow and N. S. Peachey. The subretinal microphotodiode array retinal prosthesis. Ophthalmic Res. Vol. 30, pgs. 195-196 (1998).

4. A. Roorda and D. R. Williams. The arrangement of the three cone .n the livin human e e. Nature Vol. 397, s. 520-522 (1999).

5. C. A. Curcio, K. R. Sloan, R. E. Kalina, and A. E. Hendrickson. Human 10 photoreceptor topography. The Journal of Comparative Neurology, Vol. 292, pgs. 497-523 (1990).

6. D. J. Mooney. Tissue Engineering with Biodegradable Poymer Matrices. Proceeding of the 1996 Fifteen Southern Biomedical Engineering Conference, Cat. No. 96TH8154, Pgs. 537-540.

7. L. Lu, C. A. Garcia and A. G. Mikos. In vitro degradation of thin poly(DL-lactic-co-glycolic acid) films. Biomed. Mater. Res. Vol. 46, pgs. 236-244 (1999).

8. L. Lu. Modulation of cell morphology and function using synthetic biodegradable polymers. Ph.D. thesis, Rice University, Houston, Tex. (May 1999).

9. J. Wyatt and J. Rizzo. Ocular implants for the blind. IEEE Spectrum, pgs. 47-53 (May 1996).

10. G. Peyman, A. Y. Chow, C. Liang, V. Chow, J. I. Perlman and N. S. Peachey. Subretinal semiconductor microphotodiode array. Ophthalmic snrgery and Lasers. Vol. 29(3), pgs. 234-241 (1998).

11. E. Zrenner, K D. Miliczid, V. P. Gabel, H. G. Graf, E. Guenther, H. Haefflinger, K Lohler, W. Nisch, M. Schubert, A. Stett, and S. Weiss. The development of subretinal microphotodiodes for replacement of degenerated photoreceptors. Ophthalmic Res. Vol. 29, pgs. 269-280 (1997).

12. N. J. Wu and A. Ignatiev. Treating Retinal Damage by Implanting Thin Film Optical Detectors. U.S. Pat. No. 5,873, 901 (Issued: Feb. 23, 1999).

13. W. Gombotz, D. Pettit, S. Pankey, J. Lawter, W. J. Huang. Prolonged Release of GM-CSF drugs (by encapsulation in microparticles of biodegradable poly lactic acid and poly glycolic acid and their copolymers). U.S. Pat. No. 5,942, 253.

14. W. Gombotz, D. Pettit, S. Pankey, J. Lawter, W. J. Huang. Prolonged Release of GM-CSF drugs (by encapsulation in microparticles of biodegradable poly lactic acid and poly glycolic acid and their copolymers). U.S. Pat. No. 6,120, 807.

15. A. Y. Chow and V. Y. Chow, "Subretinal Electrical Stimulation of the Rabbit Retina", Neuroscience Letters, vol. 225, pp 13-16, 1997.

16. P. S. Brody, "Large polarization dependent photovoltages in ceramic $BaTiO_3$+5 wt. % $CaTiO_3$", Solid State communication, vol. 12, pp 673-676, 1973.

17. V. M. Fridkin, "Photo-ferroelectrics", Springer Series in Solid State Science vol 9, Springer-Verlag Berlin Heidelberg New York, chapter 6, pp 85-117. 1979

18. W. K. Purves, G. H. Orians, and H. C. Heller, "Life: The Science of Biology", Forth Edition, Sinaver Associates, Inc. W.H. Freeman and Company. Chapter 39, pp. 894-903, 1995

Any patents or publications mentioned in this specification are indicative of the levels of those skilled in the art to which the invention pertains. These patents and publications are herein incorporated by reference to the same extent as if each individual publication was indicated to be incorporated by reference specifically and individually.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

We claimed:

1. An implant for conmnunicating optical information to retinal neurons in an comprising a bio-erodible carrier and a patterned plurality of optically active, thin film heterostructure optical microdetectors, where each microdetector converts light energy into electrical energy sufficient to activate bipolar cells of a retinal site for transmission of the optical information to the brain and where the pattern is designed to mimic a pattern of cones and/or rods in the retinal site.

2. The implant of claim 1, further comprising a first plurality of optically active, thin film heterostructure optical microdetectors sensitive to light in a low energy range or red range of the visible light energy range of the electromagnetic spectrum (RMDs), a second plurality of optically active, thin film heterostructure optical microdetectors sensitive to light in a medium energy range or green range of the visible light energy range of the electromagnetic spectrum (GMDs), a third plurality of optically active, thin film heterostracture optical microdetectors sensitive to light in a high energy range or blue range of the visible light energy range of the electromagnetic spectrum (BMDs), where the three microdetectors are arranged in a pattern with distributions of RMDs, GMDs and BMDs similar to a red, green, blue cone cell distributions in a retinal site into which the implant is to be implanted and where each microdetector converts light energy into electrical energy sufficient to activate bipolar cells in the retinal site.

3. The implant of claim 1, wherein the optically active heterostructure comprises a bottom electrode layer and an optically active layer thereon, where the bottom electrode layer comprises platinum, gold, $LaSrCoO_3$, $RuO_2$, or $IrO_2$ doped $CeO_2$ or mixtures or combinations thereof and where the optically active layer comprises an oxide or a nitride.

4. The implant of claim 1, wherein the biodegradable polymer is polyglycolic acid, poly-l-lactide, poly-dl-lactide, caprolactane, dl-lactic-co-glycolic-acid or other co-polymers thereof or mixtures or combinations thereof.

5. The implant of claim 1, wherein each microdetector in the array has a diameter of about 5 microns to about 500 microns.

6. The implant of claim 1, wherein the active heterostructure further comprises a top conducting layer.

7. The implant of claim 3, wherein the optically active oxide or nitride layer is selected from the group consisting of ferroelectric Perovskite oxides including $PbZrTiO_3$, $BaTiO_3$, $BaSrTiO_3$, ZnO, $BiVMgO_3$, GaN, BN, and mixtures or combinations thereof.

8. The implant of claim 3, wherein the optically active heterostructure further comprises a top electrode comprising platinum, gold, $LaSrCoO_3$, $RuO_2$, $IrO_2$ doped $CeO_2$, or other conducting oxide or mixtures or combinations thereof.

9. The implant of claim 7, wherein the perovskite is doped and is $PbZrTiO_3$ wherein the dopant comprises La, Nb, Sb, Mn, or Ca or mixtures or combinations thereof.

* * * * *